(12) United States Patent
Sakurada et al.

(10) Patent No.: US 6,312,949 B1
(45) Date of Patent: Nov. 6, 2001

(54) REGULATION OF TYROSINE HYDROXYLASE EXPRESSION

(75) Inventors: Kazuhiro Sakurada; Theo Palmer, both of San Diego; Fred H. Gage, La Jolla, all of CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/277,078

(22) Filed: Mar. 26, 1999

(51) Int. Cl.$^7$ .............................. C12N 15/63; C12N 5/00; C12N 9/02

(52) U.S. Cl. ............................ 435/325; 435/6; 435/69.1; 435/455; 435/183; 435/189; 435/368; 536/23.1

(58) Field of Search ................................. 435/455, 6, 183, 435/189, 69.1, 325, 368; 536/23.1

(56) References Cited

FOREIGN PATENT DOCUMENTS

WO 94/04675 * 3/1994 (WO) .

OTHER PUBLICATIONS

Nakagawa et al., Roles of cell autonomous mechanisms for differential expression of region–specific transcription factors in neuroepithelial cells, Development 122: 2449–2464, 1996.*
Scearce et al., RNR–1, a Nuclear Receptor in the NGFI–B/Nur77 Family That Is Rapidly Induced in Regenerating Liver, J. Biol. Chem. 268(12): 8855–8861, Apr. 1993.*
Castillo et al. Dopamine Biosynthesis Is Selectively Abolished in Substantia Nigra/Ventral Tegumental Area but Not in Hypothalmic Neurons in Mice with Targeted Disruption on the Nurr1 Gene, Mol. Cell. Neuroscience 11: 36–46, Mar. 1998.*
Law et al. Identification of a New Brain–Specific Transcription Factor, NURR1, Mol. Endocrinol. 6(12): 2129–2135, 1992.*

* cited by examiner

Primary Examiner—Rebecca E. Prouty
Assistant Examiner—Richard Hutson
(74) Attorney, Agent, or Firm—Knobbe, Martens, Olson & Bear, LLP

(57) ABSTRACT

The invention relates to methods and materials involved in the regulation of tyrosine hydroxylase expression as well as the treatment of catecholamine-related diseases. Specifically, the invention provides cells that contain exogenous nucleic acid having a nucleic acid sequence that encodes Nurr1 as well as methods and materials for inducing tyrosine hydroxylase expression, treating catecholamine-related deficiencies, and identifying tyrosine hydroxylase-related deficiencies.

10 Claims, 15 Drawing Sheets

Shh During Differentiation
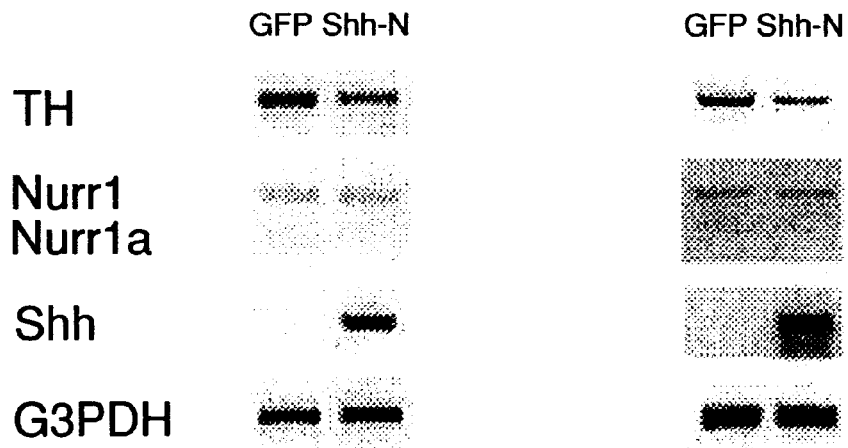
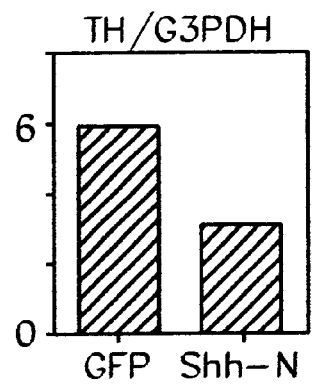
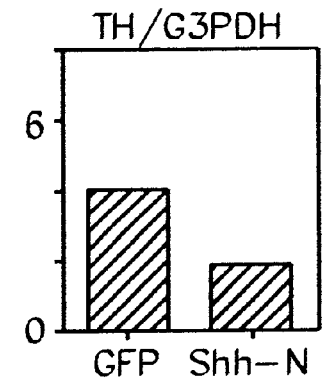
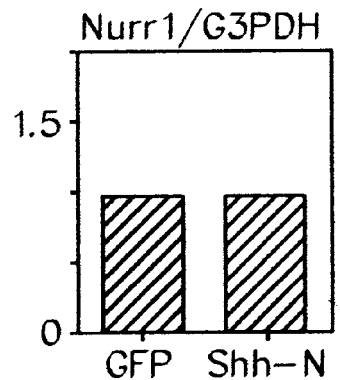
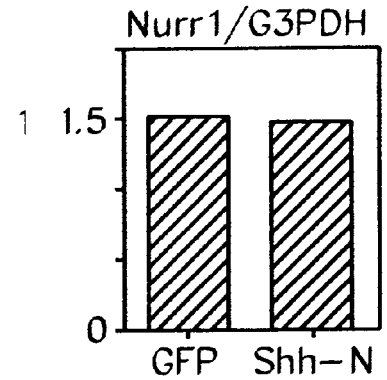
*FIG. 3A*    *FIG. 3B*

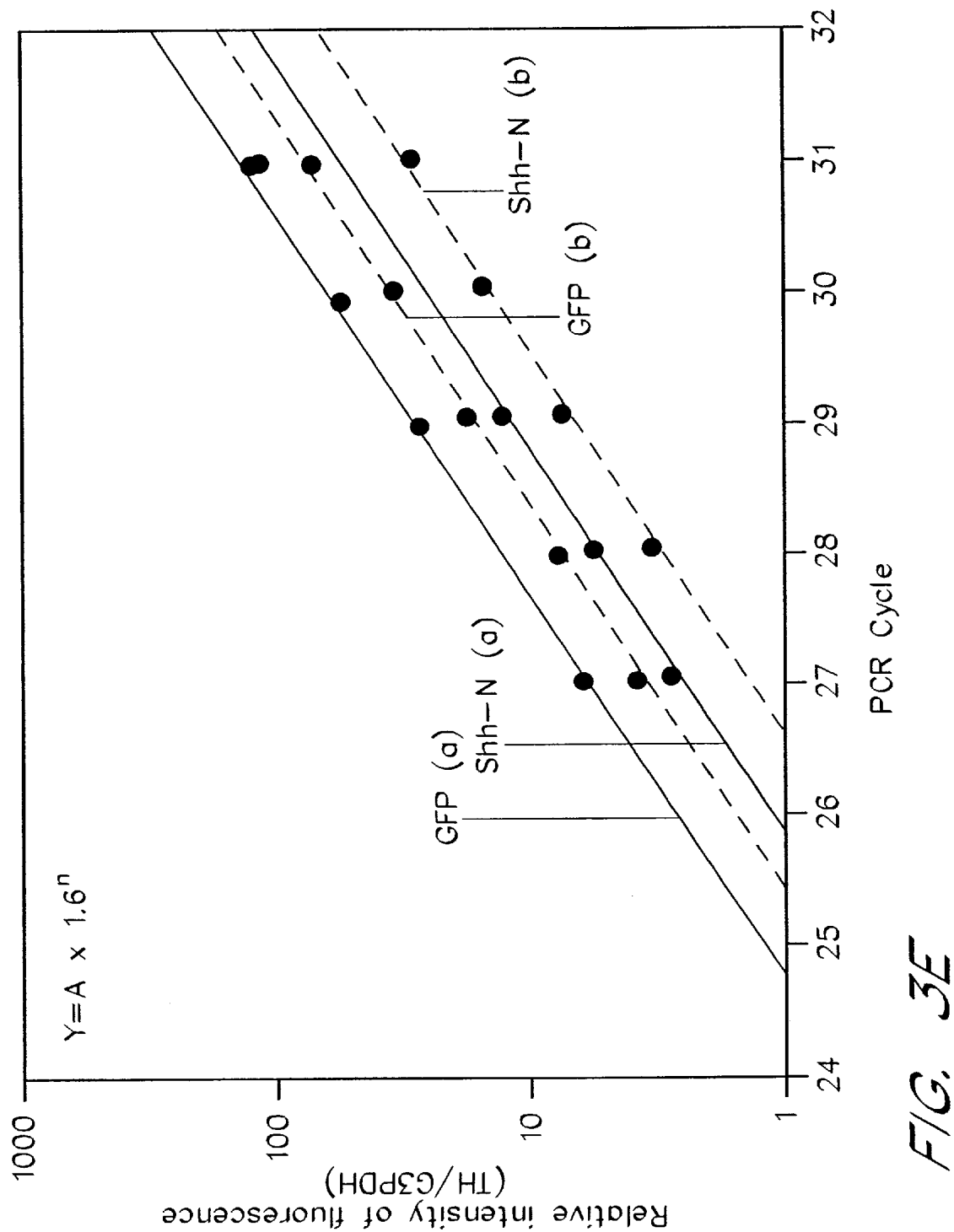

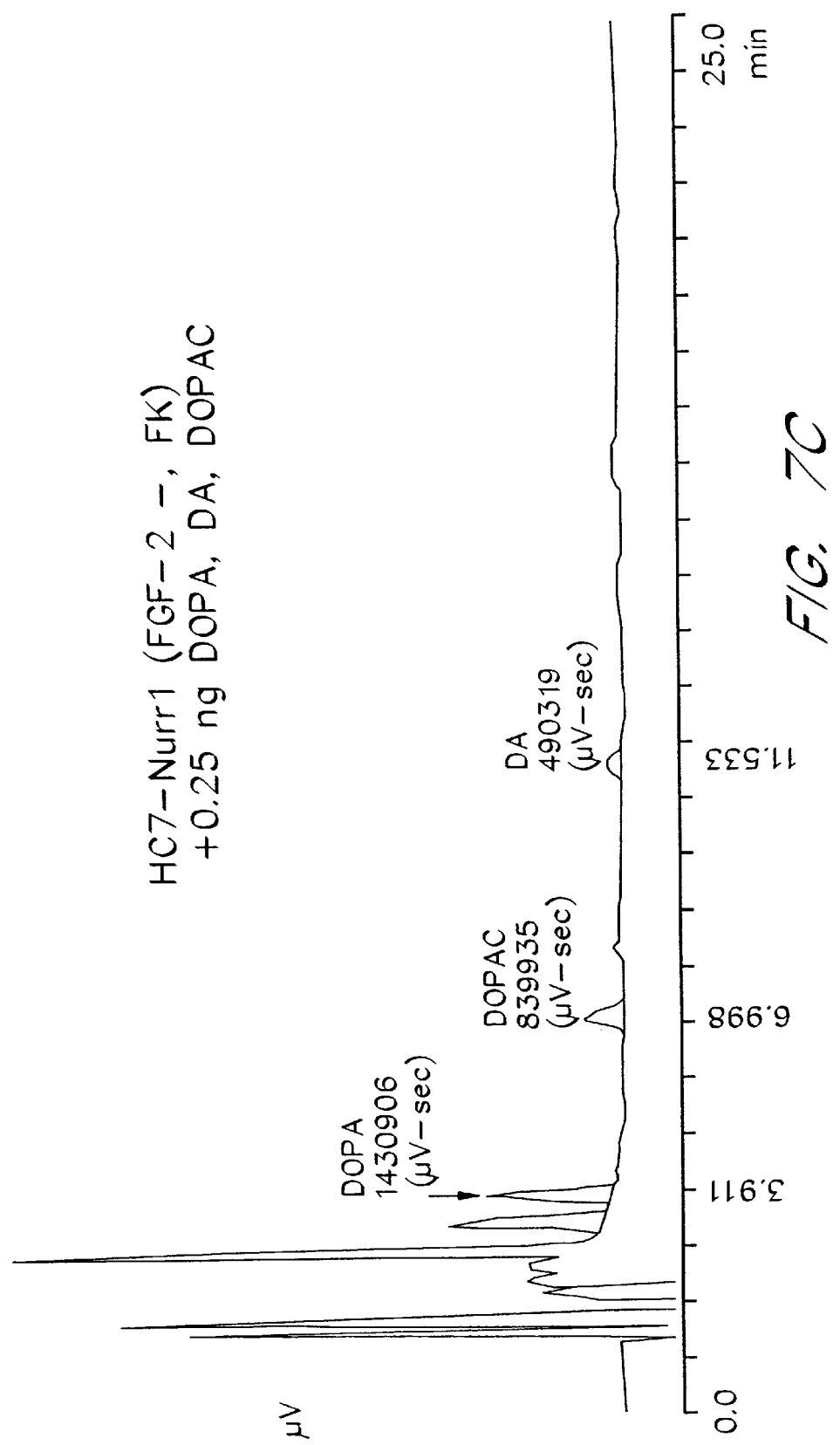

SEQUENCE LISTING

<160> NUMBER OF SEQ ID NOS: 60

<210> SEQ ID NO 1
<211> LENGTH: 1797
<212> TYPE: DNA
<213> ORGANISM: Rattus norvegicus
<220> FEATURE:
<221> NAME/KEY: CDS
<222> LOCATION: (1)...(900)

<400> SEQUENCE: 1

| | | | | | | | | | | | | | | | | |
|---|---|---|---|---|---|---|---|---|---|---|---|---|---|---|---|---|
| atg | cct | tgt | gtt | cag | gcg | cag | tat | ggg | tcc | tcg | cct | caa | gga | gcc | agc | 48 |
| Met | Pro | Cys | Val | Gln | Ala | Gln | Tyr | Gly | Ser | Ser | Pro | Gln | Gly | Ala | Ser | |
| 1 | | | | 5 | | | | | 10 | | | | | 15 | | |

| ccc | gct | tct | cag | agc | tac | agt | tac | cac | tct | tcg | gga | gaa | tac | agc | tcc | 96 |
|---|---|---|---|---|---|---|---|---|---|---|---|---|---|---|---|---|
| Pro | Ala | Ser | Gln | Ser | Tyr | Ser | Tyr | His | Ser | Ser | Gly | Glu | Tyr | Ser | Ser | |
| | | | 20 | | | | | 25 | | | | | 30 | | | |

| gat | ttc | tta | act | cca | gag | ttt | gtc | aag | ttt | agc | atg | gac | ctc | acc | aac | 144 |
|---|---|---|---|---|---|---|---|---|---|---|---|---|---|---|---|---|
| Asp | Phe | Leu | Thr | Pro | Glu | Phe | Val | Lys | Phe | Ser | Met | Asp | Leu | Thr | Asn | |
| | | 35 | | | | | 40 | | | | | 45 | | | | |

| act | gaa | att | act | gcc | acc | act | tct | ctc | ccc | agc | ttc | agt | acc | ttt | atg | 192 |
|---|---|---|---|---|---|---|---|---|---|---|---|---|---|---|---|---|
| Thr | Glu | Ile | Thr | Ala | Thr | Thr | Ser | Leu | Pro | Ser | Phe | Ser | Thr | Phe | Met | |
| 50 | | | | | 55 | | | | | 60 | | | | | | |

| gac | aac | tac | agc | aca | ggc | tac | gac | gtc | aag | cca | cct | tgc | ttg | tac | caa | 240 |
|---|---|---|---|---|---|---|---|---|---|---|---|---|---|---|---|---|
| Asp | Asn | Tyr | Ser | Thr | Gly | Tyr | Asp | Val | Lys | Pro | Pro | Cys | Leu | Tyr | Gln | |
| 65 | | | | 70 | | | | | 75 | | | | | 80 | | |

| atg | ccc | ctg | tcc | gga | cag | cag | tcc | tcc | att | aag | gta | gaa | gac | att | cag | 288 |
|---|---|---|---|---|---|---|---|---|---|---|---|---|---|---|---|---|
| Met | Pro | Leu | Ser | Gly | Gln | Gln | Ser | Ser | Ile | Lys | Val | Glu | Asp | Ile | Gln | |
| | | | | 85 | | | | | 90 | | | | | 95 | | |

| atg | cac | aac | tac | cag | caa | cac | agc | cac | ctg | ccc | cct | cag | tcc | gag | gag | 336 |
|---|---|---|---|---|---|---|---|---|---|---|---|---|---|---|---|---|
| Met | His | Asn | Tyr | Gln | Gln | His | Ser | His | Leu | Pro | Pro | Gln | Ser | Glu | Glu | |
| | | | 100 | | | | | 105 | | | | | 110 | | | |

| atg | atg | cca | cac | agc | ggg | tcg | gtt | tac | tac | aag | ccc | tct | tcg | ccc | ccg | 384 |
|---|---|---|---|---|---|---|---|---|---|---|---|---|---|---|---|---|
| Met | Met | Pro | His | Ser | Gly | Ser | Val | Tyr | Tyr | Lys | Pro | Ser | Ser | Pro | Pro | |
| | | 115 | | | | | 120 | | | | | 125 | | | | |

| aca | ccc | agc | acc | ccg | ggc | ttc | cag | gtg | cag | cat | agc | ccg | atg | tgg | gac | 432 |
|---|---|---|---|---|---|---|---|---|---|---|---|---|---|---|---|---|
| Thr | Pro | Ser | Thr | Pro | Gly | Phe | Gln | Val | Gln | His | Ser | Pro | Met | Trp | Asp | |
| | 130 | | | | | 135 | | | | | 140 | | | | | |

| gat | ccg | ggc | tcc | ctt | cac | aac | ttc | cac | cag | aac | tac | gtg | gcc | act | acg | 480 |
|---|---|---|---|---|---|---|---|---|---|---|---|---|---|---|---|---|
| Asp | Pro | Gly | Ser | Leu | His | Asn | Phe | His | Gln | Asn | Tyr | Val | Ala | Thr | Thr | |
| 145 | | | | | 150 | | | | | 155 | | | | | 160 | |

| cat | atg | atc | gag | cag | agg | aag | aca | cct | gtc | tcc | cgc | ctt | tca | ctc | ttc | 528 |
|---|---|---|---|---|---|---|---|---|---|---|---|---|---|---|---|---|
| His | Met | Ile | Glu | Gln | Arg | Lys | Thr | Pro | Val | Ser | Arg | Leu | Ser | Leu | Phe | |
| | | | 165 | | | | | 170 | | | | | 175 | | | |

| tcc | ttt | aag | cag | tcg | ccc | ccg | ggc | act | cct | gtg | tct | agc | tgc | cag | atg | 576 |
|---|---|---|---|---|---|---|---|---|---|---|---|---|---|---|---|---|
| Ser | Phe | Lys | Gln | Ser | Pro | Pro | Gly | Thr | Pro | Val | Ser | Ser | Cys | Gln | Met | |
| | | 180 | | | | | 185 | | | | | 190 | | | | |

| cgc | ttt | gac | ggg | cct | ctg | cac | gtc | ccc | atg | aac | ccg | gag | ccc | gcg | ggc | 624 |
|---|---|---|---|---|---|---|---|---|---|---|---|---|---|---|---|---|
| Arg | Phe | Asp | Gly | Pro | Leu | His | Val | Pro | Met | Asn | Pro | Glu | Pro | Ala | Gly | |
| | 195 | | | | | 200 | | | | | 205 | | | | | |

| agc | cac | cac | gta | ctg | gat | ggg | cag | acc | ttc | gcc | gtg | ccc | aat | ccc | att | 672 |
|---|---|---|---|---|---|---|---|---|---|---|---|---|---|---|---|---|
| Ser | His | His | Val | Leu | Asp | Gly | Gln | Thr | Phe | Ala | Val | Pro | Asn | Pro | Ile | |
| 210 | | | | | 215 | | | | | 220 | | | | | | |

| cgc | aag | ccg | gca | tcc | atg | ggc | ttc | ccg | ggc | ctg | cag | atc | ggc | cac | gcg | 720 |
|---|---|---|---|---|---|---|---|---|---|---|---|---|---|---|---|---|
| Arg | Lys | Pro | Ala | Ser | Met | Gly | Phe | Pro | Gly | Leu | Gln | Ile | Gly | His | Ala | |
| 225 | | | | | 230 | | | | | 235 | | | | | 240 | |

| tcg | cag | ttg | ctt | gac | acg | cag | gtg | ccc | tcg | ccg | ccg | tcc | cgg | ggc | tct | 768 |
|---|---|---|---|---|---|---|---|---|---|---|---|---|---|---|---|---|
| Ser | Gln | Leu | Leu | Asp | Thr | Gln | Val | Pro | Ser | Pro | Pro | Ser | Arg | Gly | Ser | |
| | | | | 245 | | | | | 250 | | | | | 255 | | |

-continued

```
ccc tcc aat gag ggt ctg tgc gct gtt tgc ggt gac aac gcg gcc tgt     816
Pro Ser Asn Glu Gly Leu Cys Ala Val Cys Gly Asp Asn Ala Ala Cys
        260                 265                 270 cag cat tac ggt gtt cgc act tgt gag ggc tgc aaa ggt ttc ttt aag     864
Gln His Tyr Gly Val Arg Thr Cys Glu Gly Cys Lys Gly Phe Phe Lys
            275                 280                 285 cgc acg gtg caa aaa aac gcg aaa tat gtg tgt tta gcaataaaa           910
Arg Thr Val Gln Lys Asn Ala Lys Tyr Val Cys Leu
        290                 295             300 attgcccagt ggataagcgc cgccgaaatc gttgtcagta ctgtcggttt cagaagtgcc   970
tggctgttgg gatggttaaa gaagtggttc gcacggacag tttaaaaggc cggagaggtc  1030
gtctaccctc aaaaccgaag agcccacagg atccctctc  ccctcacct ccggtgagtc   1090
tgatcagtgc cctcgtcaga gcccacgtcg actccaatcc ggcaatgacc agcctggact  1150
attccaggtt ccaggcaaac cctgactatc agatgagtgg agatgatact caacatatcc  1210
agcagttcta cgatctcctg actggctcta tggagatcat cagagggtgg gcagagaaga  1270
ttcctggctt tgctgacctg cccaaagccg atcaggacct gctttttgaa tcagcttttct 1330
tagaattatt tgttctacgc ttagcataca ggtccaaccc agtggagggt aaactcatct  1390
tttgcaatgg ggtggtcttg cacaggttgc aatgcgtgcg tggctttggg gaatggattg  1450
attccattgt tgaattctcc tccaacttgc agaatatgaa catcgacatt tctgccttct  1510
cctgcattgc tgccctggct atggtcacag agagacacgg gctcaaggaa cccaagagag  1570
tggaagagct acaaaacaaa attgtaaatt gtcttaaaga ccatgtgact ttcaataatg  1630
ggggattgaa ccgacccaac tacctgtcca aactgttggg gaagctccca gaacttcgca  1690
cccttttgcac acagggggctc cagcgcattt tctacctgaa attggaagac ttggtaccac 1750
caccagcaat aattgacaaa ctttctcctgg acaccttacc tttctaa                1797
```

<210> SEQ ID NO 2
<211> LENGTH: 300
<212> TYPE: PRT
<213> ORGANISM: Rattus norvegicus

<400> SEQUENCE: 2

```
Met Pro Cys Val Gln Ala Gln Tyr Gly Ser Ser Pro Gln Gly Ala Ser
 1               5                  10                  15

Pro Ala Ser Gln Ser Tyr Ser Tyr His Ser Ser Gly Glu Tyr Ser Ser
            20                  25                  30

Asp Phe Leu Thr Pro Glu Phe Val Lys Phe Ser Met Asp Leu Thr Asn
        35                  40                  45

Thr Glu Ile Thr Ala Thr Thr Ser Leu Pro Ser Phe Ser Thr Phe Met
    50                  55                  60

Asp Asn Tyr Ser Thr Gly Tyr Asp Val Lys Pro Pro Cys Leu Tyr Gln
65                  70                  75                  80

Met Pro Leu Ser Gly Gln Gln Ser Ser Ile Lys Val Glu Asp Ile Gln
                85                  90                  95

Met His Asn Tyr Gln Gln His Ser His Leu Pro Pro Gln Ser Glu Glu
            100                 105                 110

Met Met Pro His Ser Gly Ser Val Tyr Tyr Lys Pro Ser Ser Pro Pro
        115                 120                 125

Thr Pro Ser Thr Pro Gly Phe Gln Val Gln His Ser Pro Met Trp Asp
    130                 135                 140

Asp Pro Gly Ser Leu His Asn Phe His Gln Asn Tyr Val Ala Thr Thr
145                 150                 155                 160
```

```
His Met Ile Glu Gln Arg Lys Thr Pro Val Ser Arg Leu Ser Leu Phe
                165                 170                 175

Ser Phe Lys Gln Ser Pro Pro Gly Thr Pro Val Ser Ser Cys Gln Met
            180                 185                 190

Arg Phe Asp Gly Pro Leu His Val Pro Met Asn Pro Glu Pro Ala Gly
        195                 200                 205

Ser His His Val Leu Asp Gly Gln Thr Phe Ala Val Pro Asn Pro Ile
    210                 215                 220

Arg Lys Pro Ala Ser Met Gly Phe Pro Gly Leu Gln Ile Gly His Ala
225                 230                 235                 240

Ser Gln Leu Leu Asp Thr Gln Val Pro Ser Pro Pro Ser Arg Gly Ser
                245                 250                 255

Pro Ser Asn Glu Gly Leu Cys Ala Val Cys Gly Asp Asn Ala Ala Cys
            260                 265                 270

Gln His Tyr Gly Val Arg Thr Cys Glu Gly Cys Lys Gly Phe Phe Lys
        275                 280                 285

Arg Thr Val Gln Lys Asn Ala Lys Tyr Val Cys Leu
    290                 295                 300

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 3
accacagtcc atgccatcac                                              20

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 4
tccaccaccc tgttgctgta                                              20

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 5
cctccttgtc tcgggctgta a                                            21

<210> SEQ ID NO 6
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 6
ctgagcttgt ccttggcgtc a                                            21

<210> SEQ ID NO 7
<211> LENGTH: 21
```

```
<212> TYPE: DNA
<213> ORGANISM: Artificial Sequence
<220> FEATURE:
<223> OTHER INFORMATION: Oligonucleotide for PCR

<400> SEQUENCE: 7
cctactggct gctcggacta a                                    21

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 8
gcgtaccagg gactcaaact c                                    21

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 9
gtgaccagaa agggcagatc c                                    21

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 10
caccggcttc ttctgggtag t                                    21

<210> SEQ ID NO 11
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 11
gcagacctca cagacgttgc t                                    21

<210> SEQ ID NO 12
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 12
aggctggttt ctcggatctg g                                    21

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 13
```
tggcgctcaa gatcgacctc a                                              21

<210> SEQ ID NO 14
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 14
cgttagggtg ggattagcgg t                                              21

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 15
taaaaggccg gagaggtcgt c                                              21

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 16
ctctcttggg ttccttgagc c                                              21

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 17
acctttggac tgcttctggg                                                20

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 18
agtcgtagcc cctgaagtgt t                                              21

<210> SEQ ID NO 19
<211> LENGTH: 19
<212> TYPE: DNA
<213> ORGANISM: Artificial Sequence
<220> FEATURE:
<223> OTHER INFORMATION: Oligonucleotide for PCR

<400> SEQUENCE: 19
gccaccctgc tcatctgga                                                 19

<210> SEQ ID NO 20
<211> LENGTH: 20
<212> TYPE: DNA
<213> ORGANISM: Artificial Sequence

```
<220> FEATURE:
<223> OTHER INFORMATION: Oligonucleotide for PCR

<400> SEQUENCE: 20
ttccggccta aacgcttctc                                                    20

<210> SEQ ID NO 21
<211> LENGTH: 22
<212> TYPE: DNA
<213> ORGANISM: Artificial Sequence
<220> FEATURE:
<223> OTHER INFORMATION: Oligonucleotide for PCR

<400> SEQUENCE: 21
catgtgtgag caagaaggtt gc                                                 22

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide for PCR

<400> SEQUENCE: 22
aagtcgagga cactggctat agg                                                23

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 23
ttctggtggc ccttgcttcc t                                                  21

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 24
tacttgctgc ggtccctgtc a                                                  21

<210> SEQ ID NO 25
<211> LENGTH: 23
<212> TYPE: PRT
<213> ORGANISM: Artificial Sequence
<220> FEATURE:
<223> OTHER INFORMATION: Amino Acid sequence representing a degenerate
      primer for PCR

<400> SEQUENCE: 25

Met Gly Ile Met Gly Ile Gly Ala Arg Met Gly Ile Ala Cys Ile Ala
 1               5                  10                  15

Cys Ile Thr Thr Tyr Ala Cys
            20

<210> SEQ ID NO 26
<211> LENGTH: 24
<212> TYPE: PRT
<213> ORGANISM: Artificial Sequence
<220> FEATURE:
<223> OTHER INFORMATION: Amino Acid representing degenerate primer for
```

```
                PCR

<400> SEQUENCE: 26

Ile Cys Lys Ile Cys Lys Arg Thr Thr Ile Asx Trp Arg Ala Ala Cys
 1               5                  10                  15

Cys Ala Ile Ala Cys Tyr Thr Gly
            20

<210> SEQ ID NO 27
<211> LENGTH: 23
<212> TYPE: PRT
<213> ORGANISM: Artificial Sequence
<220> FEATURE:
<223> OTHER INFORMATION: Amino Acid representing degenerate primer for
      PCR

<400> SEQUENCE: 27

Ala Ala Arg Met Gly Ile Cys Cys Ile Met Gly Ile Ala Cys Ile Gly
 1               5                  10                  15

Cys Ile Thr Thr Tyr Ala Cys
            20

<210> SEQ ID NO 28
<211> LENGTH: 23
<212> TYPE: PRT
<213> ORGANISM: Artificial Sequence
<220> FEATURE:
<223> OTHER INFORMATION: Amino Acid representing degenerate primer for
      PCR

<400> SEQUENCE: 28

Cys Lys Tyr Thr Thr Arg Thr Thr Tyr Thr Gly Arg Ala Ala Cys Cys
 1               5                  10                  15

Ala Asp Ala Thr Tyr Thr Thr
            20

<210> SEQ ID NO 29
<211> LENGTH: 23
<212> TYPE: PRT
<213> ORGANISM: Artificial Sequence
<220> FEATURE:
<223> OTHER INFORMATION: Amino Acid representing degenerate primer for
      PCR

<400> SEQUENCE: 29

Tyr Thr Ile Gly Ala Arg Ala Ala Arg Gly Ala Arg Thr Thr Tyr Cys
 1               5                  10                  15

Ala Tyr Thr Thr Tyr Ala Ala
            20

<210> SEQ ID NO 30
<211> LENGTH: 23
<212> TYPE: PRT
<213> ORGANISM: Artificial Sequence
<220> FEATURE:
<223> OTHER INFORMATION: Amino Acid representing degenerate primer for
      PCR

<400> SEQUENCE: 30

Thr Thr Cys Ala Thr Ile Cys Lys Ile Cys Lys Arg Thr Thr Tyr Thr
 1               5                  10                  15

Gly Arg Ala Ala Cys Cys Ala
            20
```

```
<210> SEQ ID NO 31
<211> LENGTH: 23
<212> TYPE: PRT
<213> ORGANISM: Artificial Sequence
<220> FEATURE:
<223> OTHER INFORMATION: Amino Acid representing degenerate primer for
      PCR

<400> SEQUENCE: 31

Met Gly Ile Met Gly Ile Trp Ser Ile Met Gly Ile Ala Cys Ile Ala
 1               5                  10                  15

Cys Ile Thr Thr Tyr Ala Cys
            20

<210> SEQ ID NO 32
<211> LENGTH: 24
<212> TYPE: PRT
<213> ORGANISM: Artificial Sequence
<220> FEATURE:
<223> OTHER INFORMATION: Amino Acid representing degenerate primer for PCR

<400> SEQUENCE: 32

Ile Cys Lys Ile Cys Lys Arg Thr Thr Ile Asx Trp Arg Ala Ala Cys
 1               5                  10                  15

Cys Ala Ile Ala Cys Tyr Thr Gly
            20

<210> SEQ ID NO 33
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 33
gcatcctgaa cctgtgtgcc a                                         21

<210> SEQ ID NO 34
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 34
gcagcatcct tgagtggtgt c                                         21

<210> SEQ ID NO 35
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 35
gatttgctga tgtccgccga g                                         21

<210> SEQ ID NO 36
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 36
aatcagtccc gagtaggcca g                                         21
```

<210> SEQ ID NO 37
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 37
agacagaccc aggcttcgct a                                                    21

<210> SEQ ID NO 38
<211> LENGTH: 21
<212> TYPE: DNA
<213> ORGANISM: Artificial Sequence
<220> FEATURE:
<223> OTHER INFORMATION: Oligonucleotide for PCR

<400> SEQUENCE: 38
tttccgctga tgcaatgggc g                                                    21

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide for PCR
<220> FEATURE:
<221> NAME/KEY: misc_feature
<222> LOCATION: (0)...(0)
<223> OTHER INFORMATION: n = A, T, G, or C
<220> FEATURE:
<221> NAME/KEY: misc_feature
<222> LOCATION: (0)...(0)
<223> OTHER INFORMATION: r = G or A

<400> SEQUENCE: 39
tcngagatgg agrtgatgaa                                                      20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide for PCR
<220> FEATURE:
<221> NAME/KEY: misc_feature
<222> LOCATION: (0)...(0)
<223> OTHER INFORMATION: h = A, C, or T; not G
<220> FEATURE:
<221> NAME/KEY: misc_feature
<222> LOCATION: (0)...(0)
<223> OTHER INFORMATION: d = A, G, or T; not C

<400> SEQUENCE: 40
ccaaagtchg cdatcttcat                                                      20

<210> SEQ ID NO 41
<211> LENGTH: 157
<212> TYPE: DNA
<213> ORGANISM: Rattus norvegicus
<220> FEATURE:
<221> NAME/KEY: CDS
<222> LOCATION: (1)...(157)

<400> SEQUENCE: 41 cgg cgg gag cgg acg acg ttt acg cgc tca cag ctg gac gtg ctc gag           48
Arg Arg Glu Arg Thr Thr Phe Thr Arg Ser Gln Leu Asp Val Leu Glu
 1               5                  10                  15

```
gcg ctg ttc gca aag act cgc tac cca gac atc ttc atg cgc gag gag      96
Ala Leu Phe Ala Lys Thr Arg Tyr Pro Asp Ile Phe Met Arg Glu Glu
             20                  25                  30 gtg gct ctc aag atc aac ctg ccc gag tcc aga gtc caa gtc tgg ttc     144
Val Ala Leu Lys Ile Asn Leu Pro Glu Ser Arg Val Gln Val Trp Phe
         35                  40                  45 aac aac agc cgc c                                                   157
Asn Asn Ser Arg
     50

<210> SEQ ID NO 42
<211> LENGTH: 52
<212> TYPE: PRT
<213> ORGANISM: Rattus norvegicus

<400> SEQUENCE: 42

Arg Arg Glu Arg Thr Thr Phe Thr Arg Ser Gln Leu Asp Val Leu Glu
 1               5                  10                  15

Ala Leu Phe Ala Lys Thr Arg Tyr Pro Asp Ile Phe Met Arg Glu Glu
             20                  25                  30

Val Ala Leu Lys Ile Asn Leu Pro Glu Ser Arg Val Gln Val Trp Phe
         35                  40                  45

Asn Asn Ser Arg
     50

<210> SEQ ID NO 43
<211> LENGTH: 156
<212> TYPE: DNA
<213> ORGANISM: Rattus norvegicus
<220> FEATURE:
<221> NAME/KEY: CDS
<222> LOCATION: (1)...(156)

<400> SEQUENCE: 43 aag cgg ccg cgg acg gcg ttc acg gcc gag cag ctg cag aga ctc aag      48
Lys Arg Pro Arg Thr Ala Phe Thr Ala Glu Gln Leu Gln Arg Leu Lys
 1               5                  10                  15 gcg gag ttc cag gca aac cgc tac atc acg gag cag cgg cga cag acc     96
Ala Glu Phe Gln Ala Asn Arg Tyr Ile Thr Glu Gln Arg Arg Gln Thr
             20                  25                  30 ctg gcc cag gag ctc agc ctg aac gag tcc cag atc aag atc tgg ttc    144
Leu Ala Gln Glu Leu Ser Leu Asn Glu Ser Gln Ile Lys Ile Trp Phe
         35                  40                  45 caa aac aag cga                                                    156
Gln Asn Lys Arg
     50

<210> SEQ ID NO 44
<211> LENGTH: 52
<212> TYPE: PRT
<213> ORGANISM: Rattus norvegicus

<400> SEQUENCE: 44

Lys Arg Pro Arg Thr Ala Phe Thr Ala Glu Gln Leu Gln Arg Leu Lys
 1               5                  10                  15

Ala Glu Phe Gln Ala Asn Arg Tyr Ile Thr Glu Gln Arg Arg Gln Thr
             20                  25                  30

Leu Ala Gln Glu Leu Ser Leu Asn Glu Ser Gln Ile Lys Ile Trp Phe
         35                  40                  45

Gln Asn Lys Arg
     50
```

<210> SEQ ID NO 45
<211> LENGTH: 156
<212> TYPE: DNA
<213> ORGANISM: Rattus norvegicus
<220> FEATURE:
<221> NAME/KEY: CDS
<222> LOCATION: (1)...(156)

<400> SEQUENCE: 45

```
aag cgg ccg cgg acg gcg ttt acc agc gag cag ctg ctg gag ctg gag      48
Lys Arg Pro Arg Thr Ala Phe Thr Ser Glu Gln Leu Leu Glu Leu Glu
 1               5                  10                  15 aag gaa ttc cac tgc aaa aag tac ctc tcc ctg acc gag cgc tca cag      96
Lys Glu Phe His Cys Lys Lys Tyr Leu Ser Leu Thr Glu Arg Ser Gln
             20                  25                  30 atc gcc cat gcc ctc aaa ctc agc gag gtg caa gta aaa ata tgg ttc     144
Ile Ala His Ala Leu Lys Leu Ser Glu Val Gln Val Lys Ile Trp Phe
         35                  40                  45 caa aac aag cga                                                     156
Gln Asn Lys Arg
     50
```

<210> SEQ ID NO 46
<211> LENGTH: 52
<212> TYPE: PRT
<213> ORGANISM: Rattus norvegicus

<400> SEQUENCE: 46

```
Lys Arg Pro Arg Thr Ala Phe Thr Ser Glu Gln Leu Leu Glu Leu Glu
 1               5                  10                  15

Lys Glu Phe His Cys Lys Lys Tyr Leu Ser Leu Thr Glu Arg Ser Gln
             20                  25                  30

Ile Ala His Ala Leu Lys Leu Ser Glu Val Gln Val Lys Ile Trp Phe
         35                  40                  45

Gln Asn Lys Arg
     50
```

<210> SEQ ID NO 47
<211> LENGTH: 111
<212> TYPE: DNA
<213> ORGANISM: Rattus norvegicus
<220> FEATURE:
<221> NAME/KEY: CDS
<222> LOCATION: (1)...(111)

<400> SEQUENCE: 47

```
ctg gag aag gag ttc cat ttc aac aag tac cta aca aga gcc cgc agg      48
Leu Glu Lys Glu Phe His Phe Asn Lys Tyr Leu Thr Arg Ala Arg Arg
 1               5                  10                  15 gtg gag ata gcc gcg tcc ctg caa ctc aat gag acc cag gtg aag atc      96
Val Glu Ile Ala Ala Ser Leu Gln Leu Asn Glu Thr Gln Val Lys Ile
             20                  25                  30 tgg ttc caa aac cgc                                                 111
Trp Phe Gln Asn Arg
         35
```

<210> SEQ ID NO 48
<211> LENGTH: 37
<212> TYPE: PRT
<213> ORGANISM: Rattus norvegicus

<400> SEQUENCE: 48

```
Leu Glu Lys Glu Phe His Phe Asn Lys Tyr Leu Thr Arg Ala Arg Arg
  1               5                  10                 15

Val Glu Ile Ala Ala Ser Leu Gln Leu Asn Glu Thr Gln Val Lys Ile
                 20                  25                  30

Trp Phe Gln Asn Arg
         35
```

```
<210> SEQ ID NO 49
<211> LENGTH: 111
<212> TYPE: DNA
<213> ORGANISM: Rattus norvegicus
<220> FEATURE:
<221> NAME/KEY: CDS
<222> LOCATION: (1)...(111)

<400> SEQUENCE: 49
```

```
ctg gag aag gag ttt cat ttc aac aag tac ctg tgc cgg ccg cgg cgg     48
Leu Glu Lys Glu Phe His Phe Asn Lys Tyr Leu Cys Arg Pro Arg Arg
  1               5                  10                 15 gtt gag atc gcc gcc ttg ctg gac ctc acc gaa agg cag gtc aaa gtc     96
Val Glu Ile Ala Ala Leu Leu Asp Leu Thr Glu Arg Gln Val Lys Val
                 20                  25                  30 tgg ttc caa aac cgc                                                111
Trp Phe Gln Asn Arg
         35
```

```
<210> SEQ ID NO 50
<211> LENGTH: 37
<212> TYPE: PRT
<213> ORGANISM: Rattus norvegicus

<400> SEQUENCE: 50
```

```
Leu Glu Lys Glu Phe His Phe Asn Lys Tyr Leu Cys Arg Pro Arg Arg
  1               5                  10                 15

Val Glu Ile Ala Ala Leu Leu Asp Leu Thr Glu Arg Gln Val Lys Val
                 20                  25                  30

Trp Phe Gln Asn Arg
         35
```

```
<210> SEQ ID NO 51
<211> LENGTH: 111
<212> TYPE: DNA
<213> ORGANISM: Rattus norvegicus
<220> FEATURE:
<221> NAME/KEY: CDS
<222> LOCATION: (1)...(111)

<400> SEQUENCE: 51
```

```
ctg gag aag gag ttc cat ttc aac cgc tac ctg tgc cgg ccg cgc cgc     48
Leu Glu Lys Glu Phe His Phe Asn Arg Tyr Leu Cys Arg Pro Arg Arg
  1               5                  10                 15 gtg gag atg gct aac ctg ctg aac ctc acc gaa cgc cag atc aag atc     96
Val Glu Met Ala Asn Leu Leu Asn Leu Thr Glu Arg Gln Ile Lys Ile
                 20                  25                  30 tgg ttc caa aac cgc                                                111
Trp Phe Gln Asn Arg
         35
```

```
<210> SEQ ID NO 52
<211> LENGTH: 37
<212> TYPE: PRT
<213> ORGANISM: Rattus norvegicus

<400> SEQUENCE: 52
```

```
Leu Glu Lys Glu Phe His Phe Asn Arg Tyr Leu Cys Arg Pro Arg Arg
```

```
                         1               5              10              15
Val Glu Met Ala Asn Leu Leu Asn Leu Thr Glu Arg Gln Ile Lys Ile
                20              25              30

Trp Phe Gln Asn Arg
         35
```

<210> SEQ ID NO 53
<211> LENGTH: 111
<212> TYPE: DNA
<213> ORGANISM: Rattus norvegicus
<220> FEATURE:
<221> NAME/KEY: CDS
<222> LOCATION: (1)...(111)

<400> SEQUENCE: 53

```
ctg gaa aag gaa ttt cat ttt aac agg tat ctg acc agg cgc cgt cgg      48
Leu Glu Lys Glu Phe His Phe Asn Arg Tyr Leu Thr Arg Arg Arg Arg
 1               5              10              15 att gaa atc gct cac acc ctg tgt ctg tct gag cgc cag atc aag atc      96
Ile Glu Ile Ala His Thr Leu Cys Leu Ser Glu Arg Gln Ile Lys Ile
                20              25              30 tgg ttt caa aac aaa                                                 111
Trp Phe Gln Asn Lys
         35
```

<210> SEQ ID NO 54
<211> LENGTH: 37
<212> TYPE: PRT
<213> ORGANISM: Rattus norvegicus

<400> SEQUENCE: 54

```
Leu Glu Lys Glu Phe His Phe Asn Arg Tyr Leu Thr Arg Arg Arg Arg
 1               5              10              15

Ile Glu Ile Ala His Thr Leu Cys Leu Ser Glu Arg Gln Ile Lys Ile
                20              25              30

Trp Phe Gln Asn Lys
         35
```

<210> SEQ ID NO 55
<211> LENGTH: 21
<212> TYPE: DNA
<213> ORGANISM: Artificial Sequence
<220> FEATURE:
<223> OTHER INFORMATION: Oligonucleotides for PCR

<400> SEQUENCE: 55
cgtaccagct cgcgcacaga c                                              21

<210> SEQ ID NO 56
<211> LENGTH: 21
<212> TYPE: DNA
<213> ORGANISM: Artificial Sequence
<220> FEATURE:
<223> OTHER INFORMATION: Oligonucleotides for PCR

<400> SEQUENCE: 56
gggaatcagc cgtcagattt g                                              21

<210> SEQ ID NO 57
<211> LENGTH: 20
<212> TYPE: DNA
<213> ORGANISM: Artificial Sequence
<220> FEATURE:
<223> OTHER INFORMATION: Oligonucleotides for PCR

```
<400> SEQUENCE: 57
tcggctgaag ccatgccttg                                              20

<210> SEQ ID NO 58
<211> LENGTH: 20
<212> TYPE: DNA
<213> ORGANISM: Artificial Sequence
<220> FEATURE:
<223> OTHER INFORMATION: Oligonucleotides for PCR

<400> SEQUENCE: 58
gacgtgcatg ggagaaagtc                                              20

<210> SEQ ID NO 59
<211> LENGTH: 21
<212> TYPE: DNA
<213> ORGANISM: Artificial Sequence
<220> FEATURE:
<223> OTHER INFORMATION: Oligonucleotides for PCR

<400> SEQUENCE: 59
catggagttt gggctgcttg g                                            21

<210> SEQ ID NO 60
<211> LENGTH: 19
<212> TYPE: DNA
<213> ORGANISM: Artificial Sequence
<220> FEATURE:
<223> OTHER INFORMATION: Oligonucleotides for PCR

<400> SEQUENCE: 60
tcacaccggc cgttccacg                                               19
```

REGULATION OF TYROSINE HYDROXYLASE EXPRESSION

BACKGROUND

1. Technical Field

The invention relates generally to neural progenitor cells and more specifically to the regulation of tyrosine hydroxylase expression and treatment of catecholamine-related diseases.

2. Background Information

During development, neural stem cells differentiate into the different types of neurons and glia found in the adult central nervous system (CNS) and peripheral nervous system (PNS). In general, these different types of neurons are classified based on the particular types of neurotransmitters they produce. For example, dopaminergic neurons produce dopamine, while noradrenergic neurons produce norepinephrine. The neurotransmitters dopamine and norepinephrine belong to a class of compounds called catecholamines. A catecholamine is an ortho-dihydroxyphenylalkylamine that is derived from the common cellular metabolite tyrosine. For example, the catecholamines dopamine and norepinephrine are synthesized from tyrosine as follows: tyrosine is converted to dihydroxyphenylalamine (DOPA) by the enzyme tyrosine hydroxylase (TH), DOPA to dopamine by the enzyme aromatic L-amino acid decarboxylase (AADC), and dopamine to norepinephrine by the enzyme dopamine β-hydroxylase (DBH). The rate limiting step for both dopamine and norepinephrine synthesis is the conversion of tyrosine into DOPA by TH. In addition, dopamine can be converted to dihydroxyphenylacetic acid (DOPAC) by the enzymes monoamine oxidase (MAO) and aldehyde dehydrogenase.

The exact mechanisms that regulate neuronal phenotype or even neuronal cell fate determination are not well understood. Developmental studies, however, have identified some genes that appear involved. Briefly, vertebrate nervous systems develop in stereotypic positions along the dorso-ventral (D-V) and anterior-posterior (A-P) axes of the neural tube (Tanabe et al., *Science* 274:1115–1123 (1996)). Transplantation and explant culture studies confirmed that signaling centers instruct cell fates along the A-P and D-V axes. A characteristic common to these centers is the interaction of receptor-ligand pairs to modify cell fate. Sonic hedgehog (Shh) and bone morphogenetic protein (BMP) are two such polypeptides that regulate cell fate along the D-V axis. Fibroblast growth factor-2 (FGF-2), FGF-8, retinoic acid (RA), and Wnt1 influence cell fate along the A-P axis. In each case, signaling induces downstream changes that are reflected in the patterning of transcription factor expression (Crossley et al., *Nature* 380:66–68 (1996); Lumsden and Krumlauf, *Science* 274:1109–1114 (1996); Shimamura et al., *Development* 124:2709–2718 (1997); and Vollmer et al, *J. Neurochem.* 71:1–19 (1998)).

Using explant cultures, intersections of Shh and FGF-8 signaling created induction sites for dopaminergic neurons in the midbrain and forebrain (Ye et al., *Cell* 93:755–766 (1998)). In addition, Nurr1, an orphan receptor belonging to the nuclear receptor superfamily (Law et al., *Mol. Endocrinol.* 6:2192–2135 (1992) and Zetterstrom et al., *Mol. Endocrinol.* 10:1656–1666 (1996)), and the bicoid-related homeobox factor Ptx3/Pitx3 (Semina et al., *Human Mol. Genet.* 6:2109–2116 (1997); Semina et al., *Nature Genet.* 19:167–170 (1998); and Smidt et al., *Proc. Natl. Acad. Sci. USA* 94:13305–13310 (1997)) appear to be involved in midbrain dopaminergic determination.

Briefly, Nurr1 is expressed at embryonic day (E) 10.5 in the ventral aspect of the mesencephalic flexure and continues to be expressed into adulthood (Zetterstrom et al., *Mol. Endocrinol.* 10:1656–1666(1996) and Zetterstrom et al., *Mol. Brain Res.* 41:111–120(1996)). Ptx3 is expressed in ventral midbrain starting at E11.5, soon after Nurr1 begins to be expressed (Smidt et al., *Proc. Natl. Acad. Sci. USA* 94:13305–13310 (1997) and Saucedo-Cawdenas et al., *Proc. Natl. Acad. Sci. USA* 95:4013–4018 (1998)). Nurr1-null mice lack midbrain dopaminergic neurons and die within 24 h after birth (Zetterstrom et al., *Science* 276:248–250 (1997); Saucedo-Cawdenas et al., *Proc. Natl. Acad. Sci. USA* 95:4013–4018 (1998); and Castillo et al., *Mol. Cell. Neurosci.* 11:36–46 (1998)). In addition, dopamine is absent in the substantia nigra and ventral tegmental area of Nurr1-null mice (Castillo et al., *Mol. Cell. Neurosci.* 11:36–46 (1998)). However, TH immunoreactivity and mRNA expression in hypothalamic, olfactory, and lower brain stem regions were unaffected, and DOPA treatments, whether given to the pregnant dams or to the newborns, failed to rescue the Nurr1-null mice (Castillo et al., *Mol. Cell. Neurosci.* 11:36–46 (1998)).

SUMMARY

The present invention relates to the regulation of tyrosine hydroxylase expression and treatment of catecholamine-related diseases. Specifically, the invention provides cells that contain exogenous nucleic acid having a nucleic acid sequence that encodes Nurr1 (SEQ ID NO:1) as well as methods and materials for inducing tyrosine hydroxylase expression, treating catecholamine-related deficiencies, and identifying tyrosine hydroxylase-related deficiencies.

The present invention is based on the discovery that expression of Nurr1 polypeptide induces tyrosine hydroxylase expression in cells derived from an adult mammal. Specifically, expression of Nurr1 polypeptide induces TH expression in both differentiated and undifferentiated adult rat-derived hippocampal progenitor cells (AHPs). In addition, AHPs overexpressing Nurr1 can produce elevated levels of DOPA and DOPAC, indicating that the TH expression induced by Nurr1 expression results in functional TH enzyme.

The present invention also is based on the discovery that Nurr1 polypeptide induces tyrosine hydroxylase expression by binding directly to the TH promoter. Specifically, Nurr1 polypeptide was found to bind directly to the TH promoter region at positions −873 to −866 (5'-AAAGGTCA-3';). Since mutations within this Nurr1-binding element of the tyrosine hydroxylase promoter region can result in reduced reporter gene expression and thus tyrosine hydroxylase-related deficiencies, such deficiencies can be identified by assessing the nucleic acid sequence within the TH promoter. Clearly, identifying a tyrosine hydroxylase-related deficiency within a mammal can provide useful information for directing medical practitioners to appropriate treatments.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DESCRIPTION OF DRAWINGS

FIG. 3 is a diagram depicting the expression of the indicated transcripts by cells expressing Shh-N.

FIG. 3A shows RT-PCR products generated from total RNA isolated from differentiated (FGF-2 withdrawal followed by 6 days of RA treatment) C31 cells that were infected 24 hours before triggering differentiation with retroviral vectors expressing either GFP or Shh-N.

FIG. 3B shows RT-PCR products generated from total RNA isolated from differentiated (FGF-2 withdrawal followed by 6 days of RA treatment), stable HC7-GFP or HC7-Shh-N cells that were treated with tetracycline until just before differentiation.

FIG. 3E shows relative intensity of fluorescence vs. PCR cycle for TH/G3PDH corresponding to FIGS. 3A and 3B.

FIG. 6 is a diagram depicting the expression of the indicated transcripts by various cells.

FIG. 7 contains three HPLC chromatograms.

FIG. 7C shows a HPLC chromatogram of the same cell lysate of Panel B spiked with a mix of DOPA, dopamine (DA), and DOPAC (50 ng/ml).

DETAILED DESCRIPTION

Figure 1:
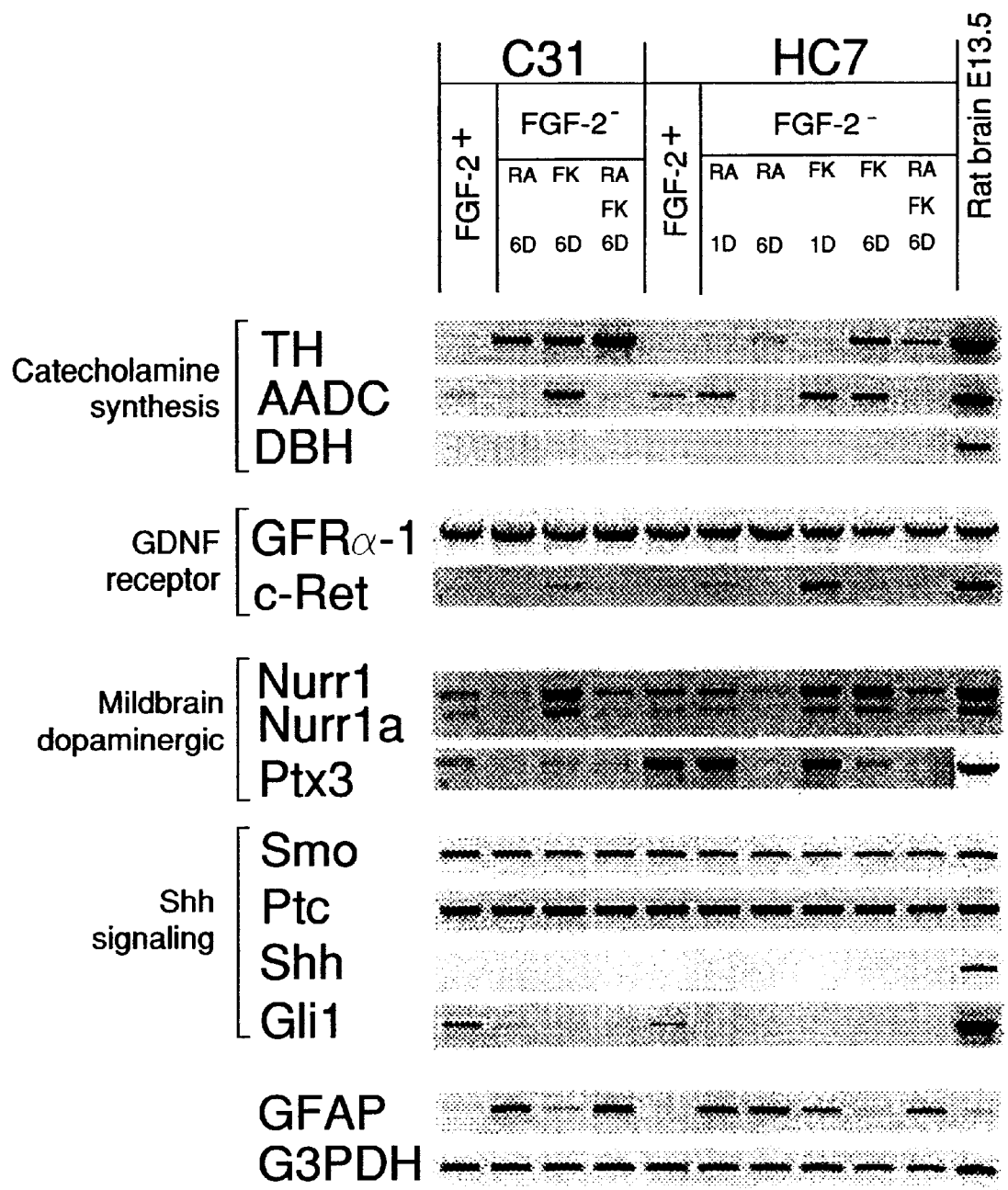
FIG. 1 is a diagram depicting the expression of the indicated transcripts by HC7 and C31 cells under proliferation (FGF-2+) and various differentiation (FGF-2−) conditions. Total RNA isolated from rat brain E13.5 was used as control.

The invention provides methods and materials related to the regulation of tyrosine hydroxylase expression as well as the treatment of catecholamine-related diseases. Specifically, the invention provides cells that contain exogenous nucleic acid as well as methods and materials for inducing tyrosine hydroxylase expression, treating catecholamine-related deficiencies, and identifying tyrosine hydroxylase-related deficiencies.

Cells containing exogenous nucleic acid that encodes Nurr1 are clinically useful, providing medical practitioners with biological material that can produce elevated levels of particular predetermined compounds such as DOPA, dopamine, norepinephrine, and DOPAC. Such cells containing exogenous Nurr1 nucleic acid can express Nurr1 polypeptide that induces TH enzyme synthesis that, in turn, results in the conversion of tyrosine into DOPA. The particular compound produced by a cell containing the exogenous Nurr1 nucleic acid can be determined based upon the set of enzymes, in addition to TH, that are expressed by that cell. For example, cells that express little to no AADC and contain exogenous Nurr1 nucleic acid can synthesize and accumulate DOPA, while cells that express AADC and DBH, and contain exogenous Nurr1 nucleic acid can synthesize and accumulate norepinephrine.

In addition, cells expressing Nurr1, and thus functional TH enzyme resulting in catecholamine production, can be used to treat catecholamine-related deficiencies associated with disease states such as Parkinson's disease, manic depression, and schizophrenia. For example, cells containing exogenous Nurr1 nucleic acid can be administered (e.g., intracranial injection) to the substantia nigra region of a Parkinson's disease patient such that those cells provide that region of the brain with dopamine. Clearly, the induction of tyrosine hydroxylase expression in a cell using an exogenous nucleic acid that encodes Nurr1 is a usefull means for creating catecholamine-producing cells that can be used in the medical treatment of catecholamine-related deficiencies.

In a first embodiment, the invention provides cells containing an exogenous nucleic acid having a nucleic acid sequence that encodes an amino acid sequence at least 65 percent identical to the rat Nurr1 amino acid sequence (Table 1; SEQ ID NO:1). Such cells are included within the scope of the invention provided the encoded amino acid sequence is expressed and induces tyrosine hydroxylase expression in that cell. Such cells include, without limitation, neural progenitor cells, neural cells, and neural stem cells. In addition, such cells may express midbrain markers such as Otx1 and En1, midbrain dopaminergic markers such as Ptx3, and any other polypeptide such as those associated with neurons and synaptic transmission. For example, a cell within the scope of the invention expresses vesicular monoamine transporters (e.g., VAMT1 and VMAT2), synaptotagmins, syntain, and/or synaptobrevin.

TABLE 1

Nucleic acid and amino acid sequence of rat Nurr1.

atgccttgtgttcaggcgcagtatgggtcctcgcctcaaggagccagccccgcttctcag agctacagttaccactcttcgggagaatacagctccgatttcttaactccagagtttgtc aagtttagcatggacctcaccaacactgaaattactgccaccacttctctcccccagcttc agtacctttatggacaactacagcacaggctacgacgtcaagccaccttgcttgtaccaa atgcccctgtccggacagcagtcctccattaaggtagaagacattcagatgcacaactac cagcaacacagccacctgcccctcagtccgaggagatgatgccacacagcgggtcggtt tactacaagccctcttcgcccccgacacccagcaccccgggcttccaggtgcagcatagc ccgatgtgggacgatccgggctcccttcacaacttccaccagaactacgtggccactacg catatgatcgagcagaggaagacacctgtctcccgcctttcactcttctcctttaagcag tcgcccccgggcactcctgtgtctagctgccagatgcgctttgacgggcctctgcacgtc cccatgaacccggagcccgcgggcagccaccacgtactggatgggcagaccttcgccgtg cccaatcccattcgcaagccggcatccatgggcttcccgggcctgcagatcggccacgcg tcgcagttgcttgacacgcaggtgccctcgccgcgtcccgGggctctccctccaatgag ggtctgtgcgctgtttgcggtgacaacgcggcctgtcagcattacggtgttcgcacttgt gagggctgcaaaggtttctttaagcgcacggtgcaaaaaaacgcgaaatatgtgtgttta gcaaataaaaattgcccagtggataagcgccgccgaaatcgttgtcagtactgtcggttt cagaagtgcctggctgttgggatggttaaagaagtggttcgcacggacagtttaaaaggc cggagaggtcgtctaccctcaaaaccgaagagcccacaggatcccctctcccccctcacct ccggtgagtctgatcagtgccctcgtcagagcccacgtcgactccaatccggcaatgacc agcctggactattccaggttccaggcaaaccctgactatcagatgagtggagatgatact caacatatccagcagttctacgatctcctgactggctctatggagatcatcagagggtgg gcagagaagattcctggctttgctgacctgcccaaagccgatcaggacctgcttttttgaa tcagctttcttagaattatttgttctacgcttagcatacaggtccaacccagtggagggt aaactcatcttttgcaatggggtggtcttgcacaggttgcaatgcgtgcgtggcttttggg gaatggattgattccattgttgaattctcctccaacttgcagaatatgaacatcgacatt tctgccttctcctgcattgctgccctggctatggtcacagagagacacgggctcaaggaa cccaagagagtggaagagctacaaaacaaaattgtaaattgtcttaaagaccatgtgact ttcaataatgggggattgaaccgacccaactacctgtccaaactgttggggaagctccca gaacttcgcacccttttgcacacaggggctccagcgcatttttctacctgaaattggaagac ttggtaccaccaccagcaataattgacaaacttttcctggacaccttacctttctaa

MPCVQAQYGSSPQGASPASQSYSYHSSGEYSSDFLTPEFVKFSMDLTNTEITATTSLPSF

STFMDNYSTGYDVKPPCLYQMPLSGQQSSIKVEDIQMNHYQQHSHLPPQSEEMMPHSGSV

YYKPSSPPTPSTPGFQVQHSPMWDDPGSLHNFHQNYVATTHMIEQRKTPVSRLSLFSFKQ

SPPGTPVSSCQMRFDGPLHVPMNPEPAGSHHVVDGQTFAVPNPIRKPASMGFPGLQIGHA

SQLLDTQVPSPPSRGSPSNEGLCAVCGDNAACQHYGVRTCEGCKGFFKRTVQKNAKYVCL

The term "progenitor cell" as used herein refers to any cell that can give rise to a distinct cell lineage through cell division. In other words, progenitor cells can be generally described as cells that give rise to differentiated cells. For example, a neural progenitor cell is a parent cell that can give rise to a daughter cell having characteristics similar to a neural cell. The term "neural cell" as used herein refers to neurons, including dopaminergic neurons as well as glial cells, including astrocytes, oligodendrocytes, and microglia. For the purpose of this invention, all neuroepithelial cells of the diencephalon, telencephalon, mesencephalon, myelencephalon, and metencephalon as well as adult hippocampal progenitor cells (AHPs), adult subventicular zone stem cells, and adult spinal cord progenitor are considered to be neural progenitor cells. In addition, all neuroepithelial cells of the mesencephalon as well as AHPs, are considered to be midbrain neural progenitor cells. Moreover, a cell within the scope of the invention can be a mammalian cell. For example, mammalian cells derived from a mammal at any stage of development from blastula formation to adult can contain an exogenous nucleic acid.

The term "nucleic acid" as used herein encompasses both RNA and DNA, including cDNA, genomic DNA, and synthetic (e.g., chemically synthesized) DNA. The nucleic acid can be double-stranded or single-stranded. Where single-stranded, the nucleic acid can be the sense strand or the antisense strand. In addition, nucleic acid can be circular or linear.

The term "exogenous" as used herein with reference to nucleic acid and a particular cell refers to any nucleic acid that does not originate from that particular cell as found in nature. Thus, all non-naturally occurring nucleic acid are considered to be exogenous to a cell once introduced into the cell. It is important to note that non-naturally occurring nucleic acid can contain nucleic acid sequences or fragments of nucleic acid sequences that are found in nature provided the nucleic acid as a whole does not exist in nature. For example, a nucleic acid containing a genomic DNA sequence within an expression vector is considered to be a non-naturally occurring nucleic acid, and thus is considered to be exogenous to a cell once introduced into the cell, since that nucleic acid as a whole (genomic DNA plus vector DNA) does not exist in nature. Thus, any vector, autonomously replicating plasmid, or virus (e.g., retrovirus, adenovirus, or herpes virus) that as a whole do not exist in nature is considered to be a non-naturally-occurring nucleic acid. It follows that genomic DNA fragments produced by PCR or restriction endonuclease treatment as well as cDNA's are considered to be a non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is considered to be a non-naturally occurring nucleic acid.

It is also important to note that a nucleic acid that is naturally occurring can be exogenous to a particular cell. For example, an entire chromosome isolated from a cell of person X would be considered an exogenous nucleic acid with respect to a cell of person Y once that chromosome is introduced into Y's cell.

Nucleic acid that is considered to be exogenous to a particular cell can be obtained using common molecular cloning or chemical nucleic acid synthesis procedures and techniques, including PCR. PCR refers to a procedure or technique in which target nucleic acid is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. Using PCR, a nucleic acid sequence can be amplified from RNA or DNA. For example, a nucleic acid sequence can be isolated by PCR amplification from total cellular RNA, total genomic DNA, and cDNA as well as from bacteriophage sequences, plasmid sequences, viral sequences, and the like. When using RNA as a source of template, reverse transcriptase can be used to synthesize complimentary DNA strands.

Standard nucleic acid sequencing techniques and software programs that translate nucleic acid sequences into amino acid sequences based on the genetic code can be used to determine whether or not a particular nucleic acid has a nucleic acid sequence that encodes an amino acid sequence at least 65 percent identical to the sequence set forth in SEQ ID NO:1. For the purpose of this invention, the percent amino acid sequence identity between the sequence set forth in SEQ ID NO:1 and any other amino acid sequence is calculated as follows. First, the two amino acid sequences are aligned using the MEGALIGN® (DNASTAR, Madison, Wis., 1997) sequence alignment software following the Jotun Heim algorithm with the default settings. Second, the number of matched positions between the two aligned amino acid sequences is determined. A matched position refers to a position in which identical residues occur at the same position as aligned by the MEGALIGN® sequence alignment software. Third, the number of matched positions is divided by 598, and the resulting value multiplied by 100 to obtain the percent identity. If the obtained percent identity is greater than or equal to 65 for a particular amino acid sequence, then that particular amino acid sequence is an amino acid sequence at least 65 percent identical to the sequence set forth in SEQ ID NO:1.

Nucleic acid having a nucleic acid sequence that encodes a polypeptide having an amino acid sequence at least 65 percent identical to the sequence set forth in SEQ ID NO:1 can be identified and obtained using any method. For example, the nucleic acid sequence set forth in SEQ ID NO:2 can be mutated using common molecular cloning techniques (e.g., site-directed mutageneses) such that the amino acid sequence encoded by the mutated nucleic acid sequence is at least 65 percent identical to the sequence set forth in SEQ ID NO: 1. Possible mutations include, without limitation, deletions, insertions, and base substitutions, as well as combinations of deletions, insertions, and base substitutions. In addition, nucleic acid and amino acid databases (e.g., GenBank®) can be used to identify a nucleic acid sequence that encodes an amino acid sequence at least 65 percent identical to the sequence set forth in SEQ ID NO:1. Briefly, any amino acid sequence having some homology to the sequence set forth in SEQ ID NO:1, or any nucleic acid sequence having some homology to the sequence set forth in SEQ ID NO:2 can be used as a query to search GenBank®. Search results then can be analyzed to determine the percent identity between the amino acid sequences obtained from an amino acid search, or the encoded amino acid sequences obtained from a nucleic acid search, and the amino acid sequence set forth in SEQ ID NO:1.

Further, PCR and nucleic acid hybridization techniques can be used to identify nucleic acid having a nucleic acid sequence that encodes a polypeptide having an amino acid sequence at least 65 percent identical to the sequence set forth in SEQ ID NO: 1. Briefly, any nucleic acid having a nucleic acid sequence that encodes an amino acid sequence at least 65 percent identical to the sequence set forth in SEQ ID NO:1, or fragment thereof, can be used as a probe to identify a similar nucleic acid by hybridization under conditions of moderate to high stringency. Such similar nucleic acid then can be isolated, sequenced, and analyzed to determine the percent identity between the encoded amino acid sequences and the amino acid sequence set forth in SEQ ID NO:1.

In general, high stringency conditions can be used to identify nucleic acid having a high degree of homology to a probe. High stringency conditions can include the use of a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, and 75 mM sodium citrate at 42° C. Another example is the use of 50% formamide, 5×SSC (0.75 M NaCl, 0.075 M sodium citrate), 50 mM sodium phosphate (pH 6.5), 0.1% sodium pyrophosphate, 5×Denhardt's solution, sonicated salmon sperm DNA (50 $\mu$g/ml), 0.1% sodium lauryl sulfate (SDS), and 10% dextan sulfate at 42° C., with washes at 42° C. in 0.2×SSC and 0.1% SDS. Alternatively, low ionic strength and high temperature can be used for washing, for example, 0.1×SSC (0.015 M NaCl/0.0015 M sodium citrate), 0.1% SDS at 65° C.

Moderate stringency conditions can be used to identify nucleic acid having a moderate degree of homology to a probe. Moderate stringency conditions can include the use of higher ionic strength and/or lower temperatures for washing of the hybridization membrane, compared to the ionic strength and temperatures used for high stringency hybridization. For example, a wash solution of 4×SSC (0.06 M NaCl/0.006 M sodium citrate), 0.1% SDS can be used at 50° C., with a last wash in 1×SSC at 65° C. Alternatively, a hybridization wash in 1×SSC at 37° C. can be used.

Low stringency conditions can be used to identify nucleic acid having a low degree of homology to a probe. Low stringency conditions can include the use of higher ionic strength and/or lower temperatures for washing of the hybridization membrane, compared to the ionic strength and temperatures used for moderate stringency hybridization. For example, a wash solution of 4×SSC (0.06 M NaCl/0.006 M sodium citrate), 0.1% SDS can be used at 37° C., with a last wash in 1×SSC at 45° C. Alternatively, a hybridization wash in 2×SSC at 37° C. can be used.

Hybridization can be done by Southern or Northern analysis to identify a DNA or RNA sequence, respectively, that hybridizes to a probe. The probe can be labeled with a radioisotope such as $^{32}$P, an enzyme, digoxygenin, or by biotinylation. The DNA or RNA to be analyzed can be electrophoretically separated on an agarose or polyacrylamide gel, transferred to nitrocellulose, nylon, or other suitable membrane, and hybridized with the probe using standard techniques well known in the art such as those described in sections 7.39–7.52 of Sambrook et al., (1989) Molecular Cloning, second edition, Cold Spring harbor Laboratory, Plainview, N.Y. Typically, a probe is at least about 20 nucleotides in length. For example, a probe corresponding to a 20 nucleotide sequence within SEQ ID NO:2 can be used to identify a nucleic acid identical to or similar to the nucleic acid sequence of SEQ ID NO:2. In addition, probes longer or shorter than 20 nucleotides can be used.

As described herein, the cells of the invention must not only contain an exogenous nucleic acid having a nucleic acid sequence that encodes an amino acid sequence at least 65 percent identical to the sequence set forth in SEQ ID NO:1, but must also express the encoded amino acid sequence such that tyrosine hydroxylase expression is induced. Methods of identifying cells that contain exogenous nucleic acid are well known to those skilled in the art. Such methods include, without limitation, PCR and nucleic acid hybridization techniques such as Northern and Southern analysis. In some cases, immunohistochemistry and biochemical techniques can be used to determine if a cell contains a particular nucleic acid by detecting the expression of a polypeptide encoded by that particular nucleic acid. For example, detection of Nurr1-immunoreactivity after introduction of an exogenous nucleic acid containing a cDNA that encodes Nurr1 into a cell that does not normally express Nurr1 polypeptide can indicate that that cell not only contains the introduced exogenous nucleic acid but also expresses the encoded Nurr1 polypeptide from that introduced exogenous nucleic acid. In this case, the detection of Nurr1 induced TH expression (e.g., increases in TH mRNA levels, TH-immunoreactivity, or TH enzymatic activity) also can indicate that that cell contains the introduced exogenous nucleic acid and expresses the encoded Nurr1 polypeptide from that introduced exogenous nucleic acid.

In addition, methods for expressing an amino acid sequence from an exogenous nucleic acid are well known to those skilled in the art. Such methods include, without limitation, constructing a nucleic acid such that a regulatory element promotes the expression of a nucleic acid sequence that encodes a polypeptide. Typically, regulatory elements are DNA sequences that regulate the expression of other DNA sequences at the level of transcription. Thus, regulatory elements include, without limitation, promoters, enhancers, and the like.

Methods of identifying cells that express an amino acid sequence from an exogenous nucleic acid also are well known to those skilled in the art. Such methods include, without limitation, immunocytochemistry, Northern analysis, and RT-PCR.

Likewise, the expression of tyrosine hydroxylase can be determined using immunocytochemistry, Northern analysis, or RT-PCR, for example. Briefly, immunocytochemistry using anti-TH antibodies can be used to assess the expression of TH polypeptide, while Northern analysis and RT-PCR techniques can be used to assess the expression of TH mRNA. Any increased expression of TH polypeptide or TH mRNA attributed to the expression of the amino acid sequence encoded by the exogenous nucleic acid is considered to be the induced TH expression. A simple comparison between TH expression results obtained from appropriate cells with and without the exogenous nucleic acid can be used to determine increases in TH expression. It is also noted that TH expression can be assessed using HPLC to measure the amount of DOPA, dopamine, norepinephrine, or DOPAC within cells, since the amount of these compounds within a cell can correlate with the expression of TH polypeptide.

The exogenous nucleic acid contained within a cell of the invention can be maintained within that cell in any form. For example, exogenous nucleic acid can be integrated into the genome of the cell or maintained in an episomal state. In other words, a cell of the invention can be a stable or transient transformant Any method can be used to introduce an exogenous nucleic acid into a cell. In fact, many methods for introducing nucleic acid into cells, whether in vivo or in vitro, are well known to those skilled in the art. For example, calcium phosphate precipitation, electroporation, heat shock, lipofection, microinjection, and viral-mediated nucleic acid transfer are common methods for introducing nucleic acid into cells. In addition, naked DNA can be delivered directly to cells in vivo as describe elsewhere (U.S. Pat. Nos. 5,580,859 and 5,589,466 including continuations thereof). Further, nucleic acid can be introduced into cells by generating transgenic animals.

Transgenic animals can be aquatic animals (such as fish, sharks, dolphin, and the like), farm animals (such as pigs, goats, sheep, cows, horses, rabbits, and the like), rodents (such as rats, guinea pigs, and mice), non-human primates (such as baboon, monkeys, and chimpanzees), and domestic animals (such as dogs and cats). Several techniques known in the art can be used to introduce nucleic acid into animals to produce the founder lines of transgenic animals. Such techniques include, but are not limited to, pronuclear microinjection (U.S. Pat. No. 4,873,191);

retrovirus mediated gene transfer into germ lines (Van der Putten et al., *Proc. Natl. Acad. Sci., USA*, 82:6148–6152 (1985)); gene transfection into embryonic stem cells (Gossler A et al., *Proc Natl Acad Sci USA* 83:9065–9069 (1986)); gene targeting into embryonic stem cells (Thompson et al., *Cell*, 56:313–321 (1989)); nuclear transfer of somatic nuclei (Schnieke AE et al., *Science* 278:2130–2133 (1997)); and electroporation of embryos.

For a review of techniques that can be used to generate and assess transgenic animals, skilled artisans can consult Gordon (*Intl. Rev. Cytol.*, 115:171–229 (1989)), and may obtain additional guidance from, for example: Hogan et al., "Manipulating the Mouse Embryo" Cold Spring Harbor Press, Cold Spring Harbor, N.Y. (1986); Krimpenfort et al., *Bio/Technology*, 9:844–847 (1991); Palmiter et al., *Cell*, 41:343–345 (1985); Kraemer et al., "Genetic Manipulation of the Early Mammalian Embryo" Cold Spring Harbor Press, Cold Spring Harbor, N.Y. (1985); Hammer et al., Nature, 315:680–683 (1985); Purscel et al., Science, 244:1281–1288 (1986); Wagner et al., U.S. Pat. No. 5,175,385; and Krimpenfort et al., U.S. Pat. No. 5,175,384.

Methods for Inducing TH Expression

As described herein, TH expression can be induced in a cell by providing a cell with an exogenous nucleic acid having a nucleic acid sequence that encodes an amino acid sequence at least 65 percent identical to the sequence set forth in SEQ ID NO:1 such that the encoded amino acid sequence is expressed. In addition, any method including those described herein can be used to introduce such an exogenous nucleic acid into a cell.

Further, a kit containing a proliferation factor and nucleic acid having a nucleic acid sequence that encodes an amino acid sequence at least 65 percent identical to the sequence set forth in SEQ ID NO:1 can be used to induce tyrosine hydroxylase expression in a cell (e.g., AHPs). A proliferation factor is any polypeptide that promotes the proliferation of cells in tissue culture including, without limitation, FGF-2, FGF4, and EGF. The proliferation factor can be used to maintain cells in a proliferative state while the nucleic acid is being introduced into the cells.

Treating Catecholamine-related Deficiencies

Catecholamine-related deficiencies in a mammal (e.g., a human patient) can be treated by administering an effective amount of cells to a mammal. The administered cells contain, as described herein, exogenous nucleic acid having a nucleic acid sequence that encodes an amino acid sequence at least 65 percent identical to the sequence set forth in SEQ ID NO:1 such that the encoded amino acid sequence is expressed and induces tyrosine hydroxylase expression. This induced TH expression causes the cells to produce a catecholamine such as dopamine or norepinephrine.

A catecholamine-related deficiency is any physical or mental condition that is associated with or attributed to an abnormal level of a catecholamine such as dopamine or norepinephrine. This abnormal level of catecholamine can be restricted to a particular region of the mammal's brain (e.g., midbrain) or adrenal gland. A catecholamine-related deficiency can be associated with disease states such as Parkinson's disease, manic depression, and schizophrenia. In addition, catecholamine-related deficiencies can be identified using clinical diagnostic procedures.

An effective amount of cells is any amount that does not cause significant toxicity to the mammal and results in either the production of a more normal level of a catecholamine or a relief, to at least some degree, of at least one clinical symptom associated with the catecholamine-related deficiency. Such an amount can be determined by assessing the clinical symptoms associated with the catecholamine-related deficiency before and after administering a fixed amount of cells. In addition, the effective amount of cells administered to a mammal can be adjusted according to the mammal's response and desired outcomes. Significant toxicity can vary for each particular patient and depends on multiple factors including, without limitation, the patient's physical and mental state, age, and tolerance to pain. The cells can be administered to any part of the mammal's body including, without limitation, midbrain, brainstem, and adrenal gland.

Catecholamine-related deficiencies also can be treated by administering an exogenous nucleic acid to a cell of the mammal. The administration can be an in vivo, in vitro, or ex vivo administration as described herein. For example, an in vivo administration can involve administering a viral vector to the midbrain region of a mammal, while an ex vivo administration can involve extracting midbrain cells from a mammal, transfecting the cells with an exogenous nucleic acid in tissue culture, and then introducing the transfected cells back into the same mammal.

Identifying TH-related Deficiencies

A tyrosine hydroxylase-related deficiency is any physiological condition characterized by a reduced level of TH expression within a cell or group of cells. Tyrosine hydroxylase-related deficiencies can be associated with disease states such as Parkinson's disease, manic depression, and schizophrenia. In addition, such deficiencies can be identified by assessing the nucleic acid sequence of Nurr1-binding elements located in the TH promoter. A Nurr1-binding element is a portion of DNA that Nurr1 polypeptide binds directly. For example, a Nurr1-binding element can be located in the TH promoter region at positions −873 to −866 (5'-AAAGGTCA-3'). Common molecular biology techniques can be used to assess the nucleic acid within the −873 to −866 region of the TH promoter for the presence or absence or mutation of this 5'-AAAGGTCA-3' sequence. For example, genomic DNA can be isolated from cells collected from a mammal and a fragment of DNA containing the −873 to −866 region of the TH promoter amplified by PCR. Once amplified, the −873 to −866 region can be sequenced and any changes to the 5'-AAAGGTCA-3' sequence determined. Murphy et al., *Gene Expression*, Vol. 5, 169–179 (1996). For example, <u>A</u>AAGGTC<u>A</u> mutation in the two underlined positions permits neural binding.

The invention will be further described in the following examples, which do not limit the scope of the invention described in the claims.

EXAMPLES

Example 1

Differentiation of Adult Neural Progenitor Cells into Midbrain Dopaminergic Neuronal Phenotype The following experimental procedures were used to isolate and propagate rat adult hippocampal progenitor cells (AHPs). Briefly, neural precursors from adult rat hippocampal formations were isolated in culture as described elsewhere (Gage et al, *Proc. Natl. Acad. Sci USA* 92:11879–1188 (1995)). Primary cultures were maintained on laminin coated dishes as described by Ray et al. (*Proc. Natl. Acad. Sci. USA* 90:3602–3606 (1993)) using DMEM:F12 (1:1) media supplemented with N2 supplement (GIBCO) and 20 ng/ml recombinant human FGF-2 from *E. coli* (provided by A. Baird. The bulk population of AHPs designated HC7 herein have been characterized elsewhere (Palmer et al., *Mol. Cell. Neurosci.* 8:389–404 (1997)). The HC7 cells were used at passages 10 through 20. The stem cell-derived clone designated C31 was isolated from the HC7 population. These cells have also been described elsewhere (Palmer et al., *Mol. Cell. Neurosci.* 8:389–404 (1997)). Both polyclonal (HC7) and clonal (C31) populations can generate a variety of neuronal phenotypes including GABA, TH, and AChE-positive neurons.

To induce differentiation, cells were initially plated onto laminin coated 6 cm dishes or coated chamber slides at a density of $2 \times 10^4$ or $10^5$ cells per $cm^2$, respectively. Cells were allowed to proliferate in N2 supplemented medium containing 20 ng/ml FGF-2 for 24 hours. FGF-2 was then withdrawn and the cells subsequently treated with N2 medium alone or with N2 medium containing 0.5 $\mu M$ retinoic acid (RA), 5 $\mu M$ forskolin (FK), or 40 ng/ml FGF-8. Medium was replaced every 48 hours.

The expression of A-P and D-V markers by the fibroblast growth factor-2 (FGF-2)-responsive AHPs was examined using RT-PCR as follows. Briefly, total RNA was isolated from cell culture using RNAzol (Tel Test). Using the Superscript preamplification system (GIBCO BRL), cDNA was made from 4 $\mu g$ of total RNA. First strand cDNA was diluted 3-fold, and 2 $\mu l$ of the diluted cDNA used for each PCR reaction. RT-PCR products were analyzed in a 1.5% agarose gel containing Ethidium Bromide (EtBr). DNA bands were photographed using an Eagle Eye XI video system (Stratagene). The image was exported in a TIFF file and DNA bands were quantified using NIH Image 1.55 software for Macintosh. The quantification value of the band was designated the absorbance (Pixels). Measurements of absorbance using the above system were linear up to 120 pixels. For quantitative PCR, cycle numbers and template quantity were determined to be in the linear range for each gene. Kinetic analyses were also used to demonstrate linearity as described elsewhere (Yokoi et al., *Biophys. Res. Commun.* 195:769–775 (1993)). Regression equations of the form: $Y = A \times E^n$, where Y is the yield of PCR products, E is the efficiency of amplification, and n is the number of cycles, were fitted to the data in the linear portion of the semilogarithmic graphs. The coefficient A was calculated for each reaction in order to estimate the relative amount of mRNA. Each sample was analyzed at least three times, and the difference in the obtained values was always less than 2%. For each experimental test condition, at least two independent experiments were performed. The following primers were used to amplify the indicated target cDNA:

```
G3PDH:   5C'-ACCACAGTCCATGCCATCAC-3'(SEQ ID NO:3)
         and 5'-TCCACCACCCTGTTGCTGTA-3'(SEQ ID NO:4)

TH:      5'-CCTCCTTGTCTCGGGCTGTAA-3'(SEQ ID NO:5)
         and 5'-CTGAGCTTGTCCTTGGCGTCA-3'(SEQ ID NO:6)

AADC:    5'-CCTACTGGCTGCTCGGACTAA-3'(SEQ ID NO:7)
         and 5'-GCGTACCAGGGACTCAAACTC-3'(SEQ ID NO:8)

DBH:     5'-GTGACCAGAAAGGGCAGATCC-3'(SEQ ID NO:9)
         and 5'-CACCGGCTTCTTCTGGGTAGT-3'(SEQ ID NO:10)

GFAP:    5'-GCAGACCTCACAGACGTTGCT-3'(SEQ ID NO:11)
         and 5'-AGGCTGGTTTCTCGGATCTGG-3'(SEQ ID NO:12)

Phox2A:  5'-TGGCGCTCAAGATCGACCTCA-3'(SEQ ID NO:13)
         and 5'-CGTTAGGGTGGGATTAGCGGT-3'(SEQ ID NO:14)

Nurr1:   5'-TAAAAGGCCGGAGAGGTCGTC-3'(SEQ ID NO:15)
         and 5'-CTCTCTTGGGTTCCTTGAGCC-3'(SEQ ID NO:16)

Ptc:     5'-ACCTTTGGACTGCTTCTGGG-3'(SEQ ID NO:17)
         and 5'-AGTCGTAGCCCCTGAAGTGTT-3'(SEQ ID NO:18)

Smo:     5'-GCCACCCTGCTCATCTGGA-3'(SEQ ID NO:19)
         and 5'-TTCCGGCCTAAACGCTTCTC-3'(SEQ ID NO:20)

Gli1:    5'-CATGTGTGAGCAAGAAGGTTGC-3'(SEQ ID NO:21)
         and 5'-AAGTCGAGGACACTGGCTATAGG-3'(SEQ ID NO:22)

Shh:     5'-TTCTGGTGGCCCTTGCTTCCT-3'(SEQ ID NO:23)
         and 5'-TACTTGCTGCGGTCCCTGTCA-3'(SEQ ID NO:24)

Otx:     5'-MGIMGIGARMGIACIACITTYAC-3'(SEQ ID NO:25)*
         and 5'-ICKICKRTTIBWRAACCAIACYTG-3'(SEQ ID NO:26)*

En:      5'-AARMGICCIMGIACIGCITTYAC-3'(SEQ ID NO:27)*
         and 5'-CKYTTRTTYTGRAACCADATYTT-3'(SEQ ID NO:28)*

Hox:     5'-YTIGARAARGARTTYCAYTTYAA-3'(SEQ ID NO:29)*
         and 5'-TTCATICKICKRTTYTGRAACCA-3'(SEQ ID NO:30)*
```

```
                            -continued
Pax:     5'-MGIMGIWSIMGIACIACITTYAC-3'(SEQ ID NO:31)*
         and 5'-ICKICKRTTIBWRAACCAIACYTG-3'(SEQ ID NO:32)*

D2R:     5'-GCATCCTGAACCTGTGTGCCA-3'(SEQ ID NO:33)
         and 5'-GCAGCATCCTTGAGTGGTGTC-3'(SEQ ID NO:34)

GFRα-1:  5'-GATTTGCTGATGTCCGCCGAG-3'(SEQ ID NO:35)
         and 5'-AATCAGTCCCGAGTAGGCCAG-3'(SEQ ID NO:36)

c-Ret:   5'-AGACAGACCCAGGCTTCGCTA-3'(SEQ ID NO:37)
         and 5'-TTTCCGCTGATGCAATGGGCG-3'(SEQ ID NO:38)

FGFR:    5'-TCNGAGATGGAGRTGATGAA-3'(SEQ ID NO:39)#
         and 5'-CCAAAGTCHGCDATCTTCAT-3'(SEQ ID NO:40)#
```

Those particular primers marked with an asterisk (*) are degenerate primers represented by the indicated amino acid sequence. For the primers marked with a pound sign (#), N represents all four bases, R represents A and G, and H represents A, T and C. The PCR products from the Ptc, Otx, En, and Hox reactions were subcloned into a TOPO-TA vector (Invitrogen) and analyzed by DNA sequencing, while the identity of each product for the remaining PCR reactions was confirmed by restriction enzyme digestion. Controls included total RNA isolated from rat brain E13.5 as well as PCR reactions lacking reverse transcriptase.

Otx1, En1, GBX2, HoxA1, HoxA2, HoxB2, HoxD3, and HoxD4 mRNA was detected in both non-clonal cultures (HC7) and stem cell-derived clonal cultures (C31) proliferating in the presence of FGF-2 (Table 2, FIG. 1). The broad range of homeobox members present indicates that AHPs are not restricted to the forebrain-specific A-P identities expected for hippocampus-derived cells. Sonic hedgehog (Shh) transcripts were not detected; however, transcripts for the Shhf receptors Ptc and Smo, and the Shh-responsive gene Gli1 were detectable in proliferating cells, suggesting some level of Shh-related signal transduction (FIG. 1). In addition, expression of midbrain (Otx1 and En1) and midbrain dopaminergic markers (Nurr1 and Ptx3) indicated that some of the AHPs may be competent to generate midbrain-specific dopaminergic neurons.

TABLE 2

Nucleotide and amino acid sequence of homeobox genes expressed in AHPs

| Gene | Nucleotide and amino acid sequence |
|---|---|
| Otx1 | CGGCGGGAGCGGACGACGTTTACGCGCTCACAGCTGGACGTGCTC<br>R  R  E  R  T  T  P  T  R  S  Q  L  D  V  L<br><br>GAGGCGCTGTTCGCAAAGACTCGCTACCCAGACATCTTCATGCGC<br>E  A  L  F  A  K  T  R  Y  P  D  I  F  M  R<br><br>GAGGAGGTGGCTCTCAAGATCAACCTGCCCGAGTCCAGAGTCCAA<br>E  E  V  A  L  K  I  N  L  P  E  S  R  V  Q<br><br>GTCTGGTTCAACAACAGCCGCC (SEQ ID NO:41)<br>V  W  F  N  N  S  R      (SEQ ID NO:42) |
| En1 | AAGCGGCCGCGGACGGCGTTCACGGCCGAGCAGCTGCAGAGACTC<br>K  R  P  R  T  A  F  T  A  E  Q  L  Q  R  L<br><br>AAGGCGGAGTTCCAGGCAAACCGCTACATCACGGAGCAGCGGCGA<br>K  A  E  F  Q  A  N  R  Y  I  T  E  Q  R  R<br><br>CAGACCCTGGCCCAGGAGCTCAGCCTGAACGAGTCCCAGATCAAG<br>Q  T  L  A  Q  E  L  S  L  N  E  S  Q  I  K<br><br>ATCTGGTTCCAAAACAAGCGA (SEQ ID NO:43)<br>I  W  F  Q  N  K  R       (SEQ ID NO:44) |
| GBX2 | AAGCGGCCGCGGACGGCGTTTACCAGCGAGCAGCTGCTGGAGCTG<br>K  R  P  R  T  A  F  T  S  E  Q  L  L  E  L<br><br>GAGAAGGAATTCCACTGCAAAAAGTACCTCTCCCTGACCGAGCGC<br>E  K  E  F  H  C  K  K  Y  L  S  L  T  E  R<br><br>TCACAGATCGCCCATGCCCTCAAACTCAGCGAGGTGCAAGTAAAA<br>S  Q  I  A  H  A  L  K  L  S  E  V  Q  V  K<br><br>ATATGGTTCCAAAACAAGCGA (SEQ ID NO:45)<br>I  W  F  Q  N  K  R       (SEQ ID NO:46) |
| HoxA1 | CTGGAGAAGGAGTTCCATTTCAACAAGTACCTAACAAGAGCCCGC<br>L  E  K  E  F  H  F  N  K  Y  L  T  R  A  R |

```
             AGGGTGGAGATAGCCGCGTCCCTGCAACTCAATGAGACCCAGGTG
             R   V   E   I   A   A   S   L   Q   L   N   E   T   Q   V

AAGATCTGGTTCCAAAACCGC (SEQ ID NO:47)
             K   I   W   F   Q   N   R   (SEQ ID NO:48)

HoxA2/B2     CTGGAGAAGGAGTTTCATTTCAACAAGTACCTGTGCCGGCCGCGG
             L   E   K   E   F   H   F   N   K   Y   L   C   R   P   R

CGGGTTGAGATCGCCGCCTTGCTGGACCTCACCGAAAGGCAGGTC
             R   V   E   I   A   A   L   L   D   L   T   E   R   Q   V

AAAGTCTGGTTCCAAAACCGC (SEQ ID NO:49)
             K   V   W   F   Q   N   R   (SEQ ID NO:50)

HoxD3        CTGGAGAAGGAGTTCCATTTCAACCGCTACCTGTGCCGGCCGCGC
             L   E   K   E   F   H   F   N   R   Y   L   C   R   P   R

CGCGTGGAGATGGCTAACCTGCTGAACCTCACCGAACGCCAGATC
             R   V   E   M   A   N   L   L   N   L   T   E   R   Q   I

AAGATCTGGTTCCAAAACCGC (SEQ ID NO:51)
             K   I   W   F   Q   N   R   (SEQ ID NO:52)

HoxD4        CTGGAAAAGGAATTTCATTTTAACAGGTATCTGACCAGGCGCCGT
             L   E   K   E   F   H   F   N   R   Y   L   T   R   R   R

CGGATTGAAATCGCTCACACCCTGTGTCTGTCTGAGCGCCAGATC
             R   I   E   I   A   H   T   L   C   L   S   E   R   Q   I

AAGATCTGGTTTCAAAACAAA (SEQ ID NO:53)
             K   I   W   F   Q   N   K   (SBQ ID NO:54)
```

Cell differentiated in the presence of RA or FK also were evaluated by immunofluorescent staining performed as described elsewhere (Gage et al., *Proc. Natl. Acad. Sci USA* 92:11879–1188 (1995)). Briefly, after fixation with 4% paraformaldehyde in PBS, cells were incubated with primary antibodies overnight at 4° C. After removing the primary antibodies, the cells were incubated overnight at 4° C. with secondary antibodies (Jackson Immunoresearch) conjugated to fluorescein isothiocyanate, cyanin-3, or cyanin-5. Primary antibody concentrations were as follows: mouse anti-MAP2ab (monoclonal, Sigma) at 1:500; mouse anti-TH (monoclonal, Boehringer Mannheim) at 1:500; rabbit anti-TH (polyclonal, Eugenetech) at 1:500; and mouse anti-AADC (monoclonal, Sigma) at 1:500. MAP2ab (microtubule-associated protein 2) is a major component of the neuronal cytoskeleton. Labeled cells were visualized using a Bio-Rad MRC1000 confocal scanning laser microscope and color images were generated using Adobe Photoshop (Adobe System). The total cell numbers were scored using nuclear counterstaining with 4',6-diamidino-2-phenylinodole (DAPI, Sigma). The relative proportions of each cell phenotype were determined by systematic sampling of 40×fields across the length and breadth of each well.

Only a small proportion of the MAP2ab-immunoreactive neurons was double labeled for TH (0.9+/−0.3% in the presence of RA and 1.5+/−0.4% in the presence of FK). Nearly all cells were immunoreactive for AADC, but none contained detectable DBH. Consistent with the immunofluorescent data, RT-PCR revealed an early upregulation of TH and AADC (at 6 days) in the absence of detectable DBH (FIG. 1) or Phox2a mRNA. DBH and Phox2a are specifically expressed in adrenergic neurons. Withdrawal of FGF-2 and treatment with FK also induced a rapid upregulation of Nurr1 mRNA expression (FIG. 1). Although RA treatment also stimulated TH expression at both the polypeptide and RNA levels, the coordinated upregulation of Nurr1 and AADC seen with FK was absent. In fact, RA had an inhibitory effect on AADC and Ptx3 mRNA expression (FIG. 1), indicating that RA and FK have overlapping yet clearly distinct effects on the signaling cascades leading to a dopaminergic phenotype.

In addition, GFRα-1, a GPI-linked GDNF binding polypeptide, was constitutively expressed under both proliferating and differentiating conditions (FIG. 1), and the receptor tyrosine kinase c-Ret, another component of the GDNF receptor, was upregulated in response to FK. Taken together, this RT-PCR data indicates that FK activates a broad transcriptional response consistent with dopaminergic rather than adrenergic or noradrenergic differentiation.

Example 2

FGF-8 Does Not Increase TH Expression When Applied During Differentiation

FGFR1, FGFR2, and FGFR3 expression was observed in AHPs, indicating that AHPs may be competent to respond to FGF-8. Since the high concentration of FGF-2 used to propagate AHPs (20 ng/ml) can activate all three FGF receptors (Omitz et al., *J. Biol. Chem.* 271:15292–15297 (1996)), the effects of exogenously applied FGF-8 might be masked in proliferating cells. Indeed, FGF-8 did not show any obvious effect on TH expression in the presence of FGF-2. FGFR3 expression, however, did increase following FGF-2 withdrawal. Thus, FGF-8 could potentially exhibit a measurable effect following FGF-2 withdrawal during the subsequent differentiation. Interestingly, FGF-8 had little effect on TH, Nurr1, or Ptx3 expression after 4 days, either in the absence or presence of FK. These results indicate that FGFR3 signaling is not important during the terminal stages of differentiation, but may instead be critical in promoting a dopaminergic competence during the early proliferative expansion of precursors. In this case, the high concentrations of FGF-2 used to maintain proliferative cultures could substitute for FGF-8 in promoting dopaminergic competence for AHPs.

Example 3

Forced Expression of Shh-N, Nurr1, Nurr1a, and Ptx3

1. Cloning of Shh-N, Nurr1, Nurr1a, and Ptx3 cDNAs containing the full open reading frames of rat Shh-N, Nurr1, Nurr1 a, and Ptx3 were cloned by RT-PCR from polyA RNA derived from Fischer 344 rat embryonic brain at embryonic day 13.5. Total RNA was isolated as described by Okayama et al. (*Methods Enzymol.* 154:3–28 (1987)). PolyA RNA was purified using Oligo(dT)-cellulose (Pharmacia) column chromatography. First strand cDNA synthesis was carried out using 50 ng of polyA RNA, Superscript II reverse transcriptase (GIBCO BRL), and oligo dT primer followed by RNase H treatment. The resulting products were PCR amplified using Pwo polymerase Boehringer Mannheim) and the following primers:

5' primer for Shh-N: 5'-CGTACCAGCTCGCGCACAGAC-3' (SEQ ID NO:55)
3' primer for Shh-N: 5'-GGGAATCAGCCGTCAGATTTG-3' (SEQ ID NO:56)
5' primer for Nurr1 and Nurr1a: 5'-TCGGCTGAAGCCATGCCTTG-3' (SEQ ID NO:57)
3' primer for Nurr1 and Nurr1a: 5'-GACGTGCATGGGAGAAAGTC-3' (SEQ ID NO:58)
5' primer for Ptx3: 5'-CATGGAGTTTGGGCTGCTTGG-3' (SEQ ID NO:59)
3' primer for Ptx3: 5'-TCACACCGGCCGTTCCACG-3' (SEQ ID NO:60)

The PCR products were subcloned into TOPO-TA cloning vector (Invitrogen) as described in the manufacturer's instructions. DNA sequencing confirmed that the clones contained the full length sequences for the rat Shh-N, Nurr1, Nurr1a, and Ptx3 coding regions.

2. Retroviral Cloning and Transduction

Figure 2:
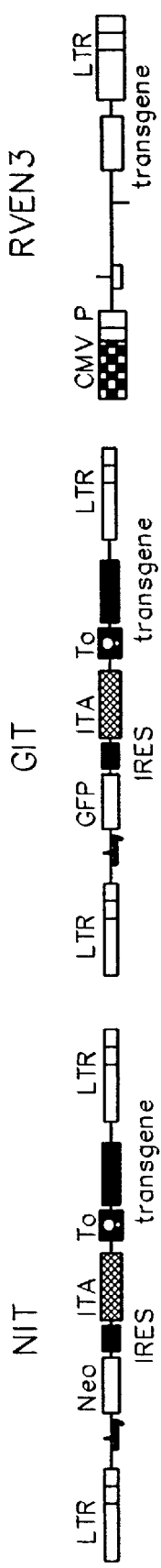
FIG. 2 is a diagram depicting the NIT, GIT, and RVEN3 retroviral vectors.

The NIT retroviral vector was constructed from LINX (Hoshimaru et al., Proc. *Natl. Acad. Sci. USA* 93:1518–1523 (1996)) by swapping positions of the tetracycline-controlled transactivator (tTA) and neomycin resistance genes (FIG. 2). The neomycin resistance gene was replaced by E-GFP coding sequence to form GIT. The transgenes within the NIT and GIT vectors are under the control of the CMV promoter fused to the tetracycline operator. RVEN3 was constructed from pCLMFG (provided by Nikunj Somia) by deleting the ATG codon between the splice acceptor site and multiple linker sites. The transgenes within the RVEN3 vector are under the control of the retrovirus LTR promoter. pCLMFG was derived from MFG and contains a hCMV immediate early promoter in place of the 5' U3 region in pCLMFG (Naviaux et al., 1996). Fragments containing Shh-N, Nurr1, Nurr1a, Ptx3, and E-GFP (Clontech) were cloned into NIT, GIT, or RVEN3 vector and the DNA transfected into producer cells (293gag pol; provided from Nikunj Somia). To increase the degree of infection of the virus, viral preparations were pseudotyped with a vesicular stomatitis virus (VSV-G) coat protein by cotransfecting the producer cells with pMD.G. Viral supernatants were concentrated by centrifugation (Burns et al., 1993) and exposed to AHPs suspensions for 30 minutes followed by plating to polyornithine/laminin-coated dishes.

To generate stable expressing cells, HC7 cells were treated with a high concentration of NIT-based viruses (multiplicity of infection=about 1) and cultured in the presence of 100 µg/ml G418. To improve cell survival during selection, medium was supplemented with conditioned medium from high density HC7 cell culture.

3. Shh-Nin Proliferating Cells Potentiates TH expression During Differentiation

The role of Shh in AHPs was examined using a tetracycline suppressible Shh-N-expressing retrovirus (NIT-SHbh-N; FIG. 2). Shh-N is a recombinant amino-terminal autoproteolytic fragment of Shh. When NIT-Shh-N was introduced into AHPs and a bulk drug resistant population of stable Shh-N-expressing cells were isolated, a high level of Shh-N mRNA expression under control of a tetracycline repressible promoter was observed.

Figures 3C, 3D:
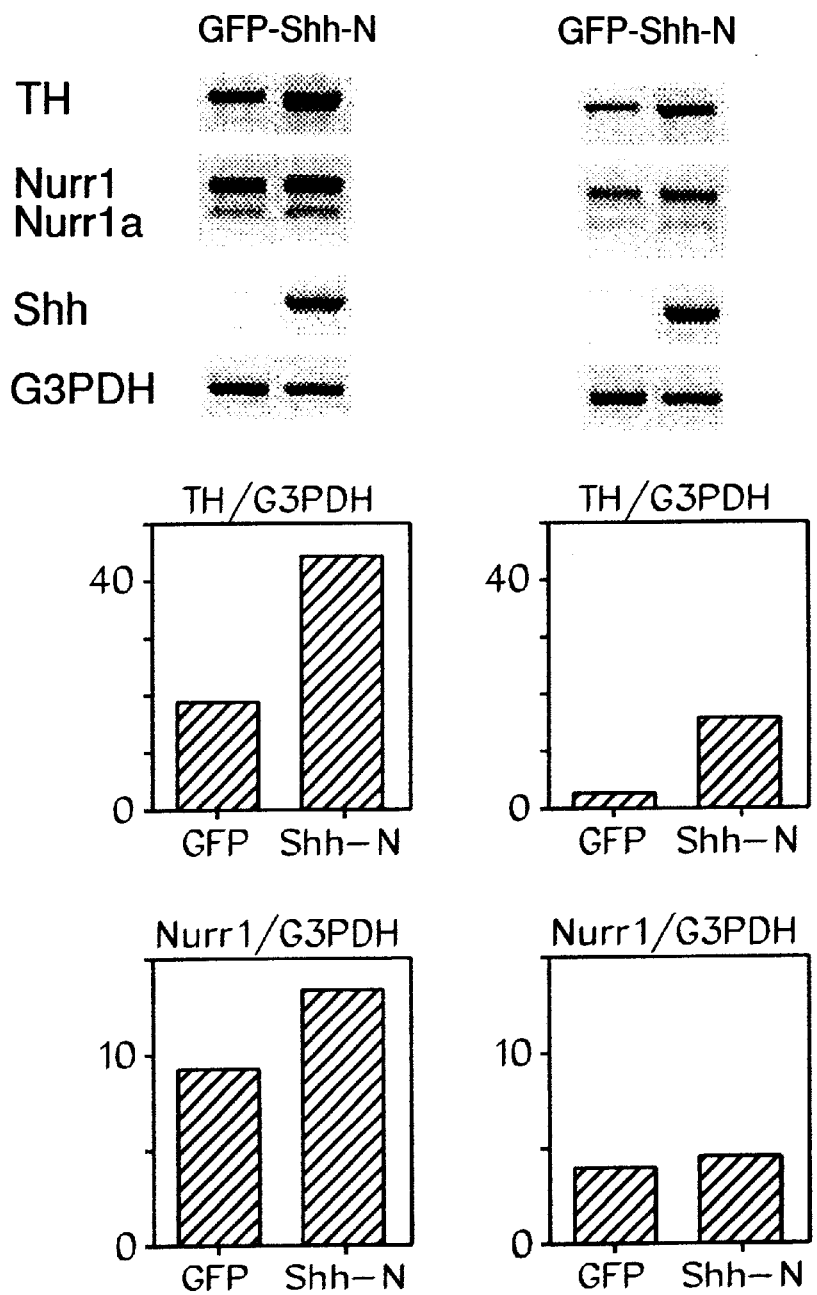
FIG. 3C shows RT-PCR products generated from total RNA isolated from differentiated (FGF-2 withdrawal followed by 6 days of FK treatment), stable HC7-GFP or HC7-Shh-N cells that were cultured without tetracycline for 10 days before differentiation.
FIG. 3D shows RT-PCR products generated from total RNA isolated from differentiated (FGF-2 withdrawal followed by 6 days of RA treatment), stable HC7-GFP or HC7-Shh-N cells that were cultured without tetracycline for ten days before differentiation.
Figure 3F:
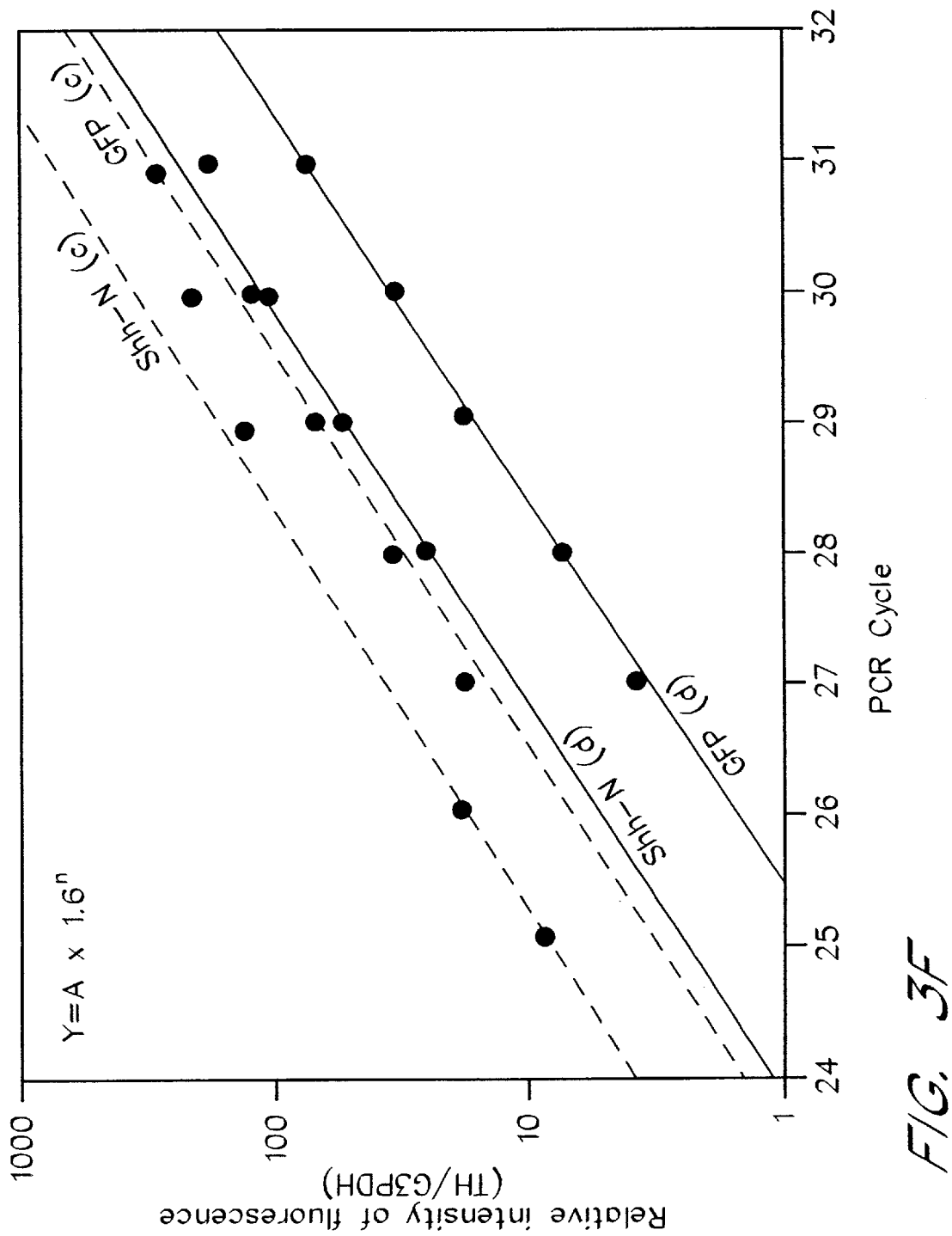
FIG. 3F shows relative intensity of fluoescence vs. PCR cycle for Th/G3PDH corresponding to FIGS. 3C and 3D. Kinetic analyses were performed as described in the specification.

To examine the effects of Shh-N expressed only during the terminal stages of differentiation, AHPs (C31) were infected with a high titer of Shh-N expressing retrovirus immediately before differentiation. Interestingly, Shh-N expression resulted in depressed TH expression after 6 days of differentiation in the presence of RA (FIG. 3, column a). Similar TH repression was observed in the stable SHH-N-expressing cells (HC7-Shh-N) when tetracycline was used to suppress Shh-N-expression until just before differentiation in the presence of RA (FIG. 3, column b). In contrast, constitutive expression of Shh-N in proliferating cells (HC7-Shh-N) for 10 days prior to differentiation resulted in a 1.8-fold and 3.7-fold increase in TH expression after 6 days of differentiation in the presence of FK or RA, respectively (FIG. 3, columns c and d). Interestingly, constitutive Shh expression had no effect on TH expression during proliferation. In addition, expression of DBH was not observed in any of these conditions. These results indicate that Shh can play an important role in the early patterning of proliferative precursors but has an inhibitory effect on TH expression when expressed during the terminal stages of differentiation.

4. Nurr1 Induces TH Expression

Figure 4A:
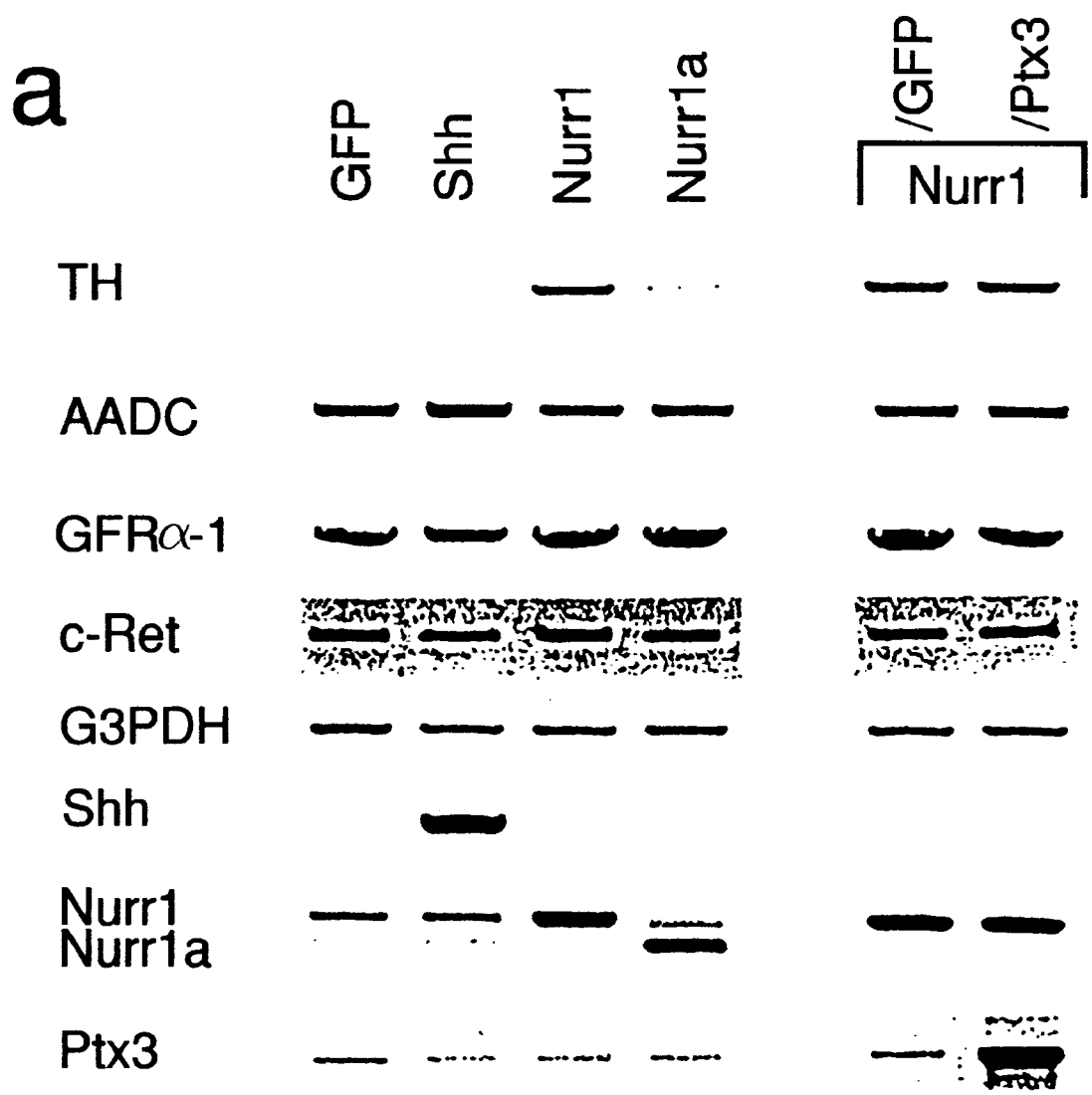
FIGS. 4a, b, and c is a diagram depicting the expression of the indicated transcripts by HC7 cells forced to express GFP, Shh-N, Nurr1, or Nurr1 a stably and HC7-Nurr1 cells forced to express GFP or Ptx3 transiently. RT-PCR products were generated from total RNA isolated from cells that were proliferating in the absence of tetracycline for two days.
Figure 4B:
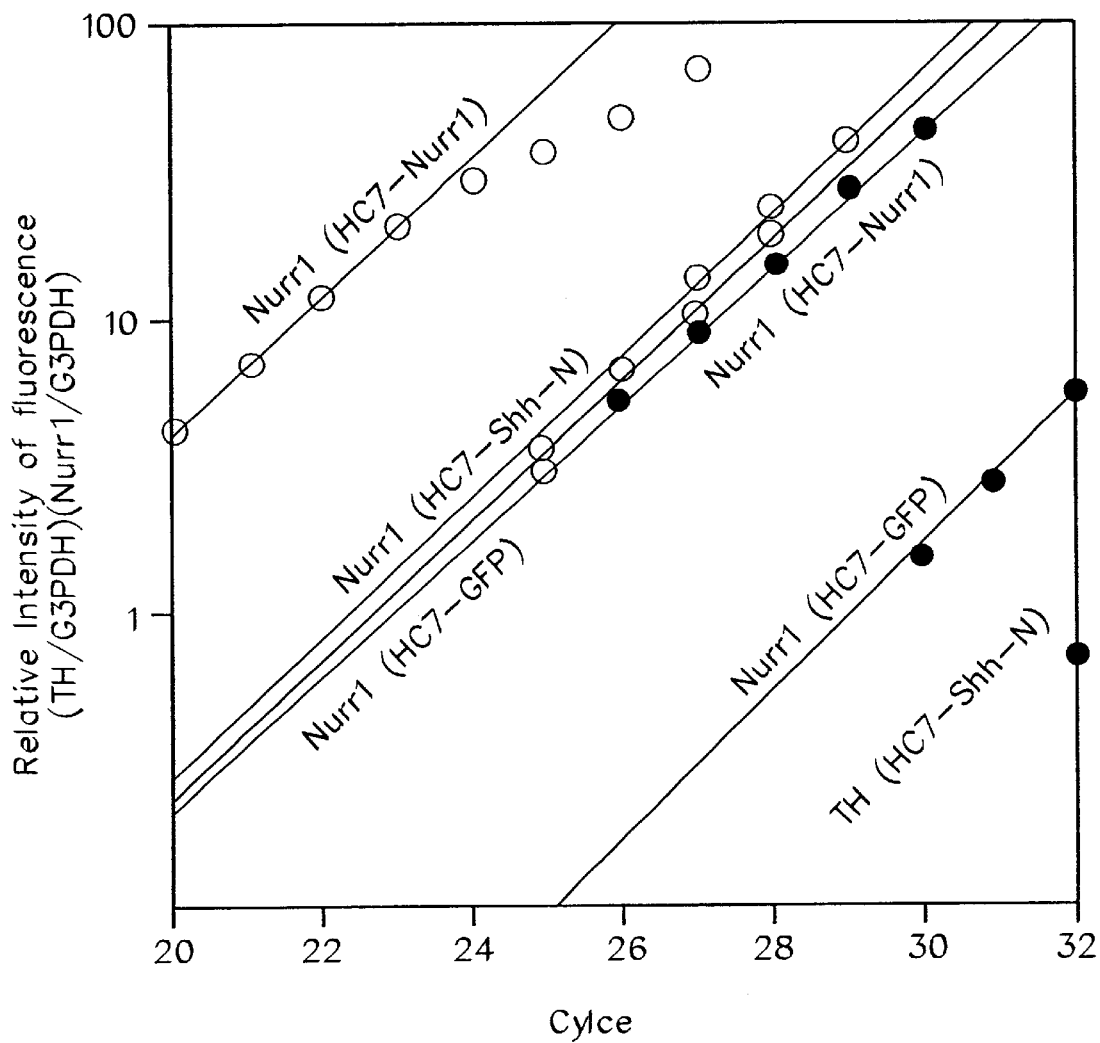
Figure 4C:
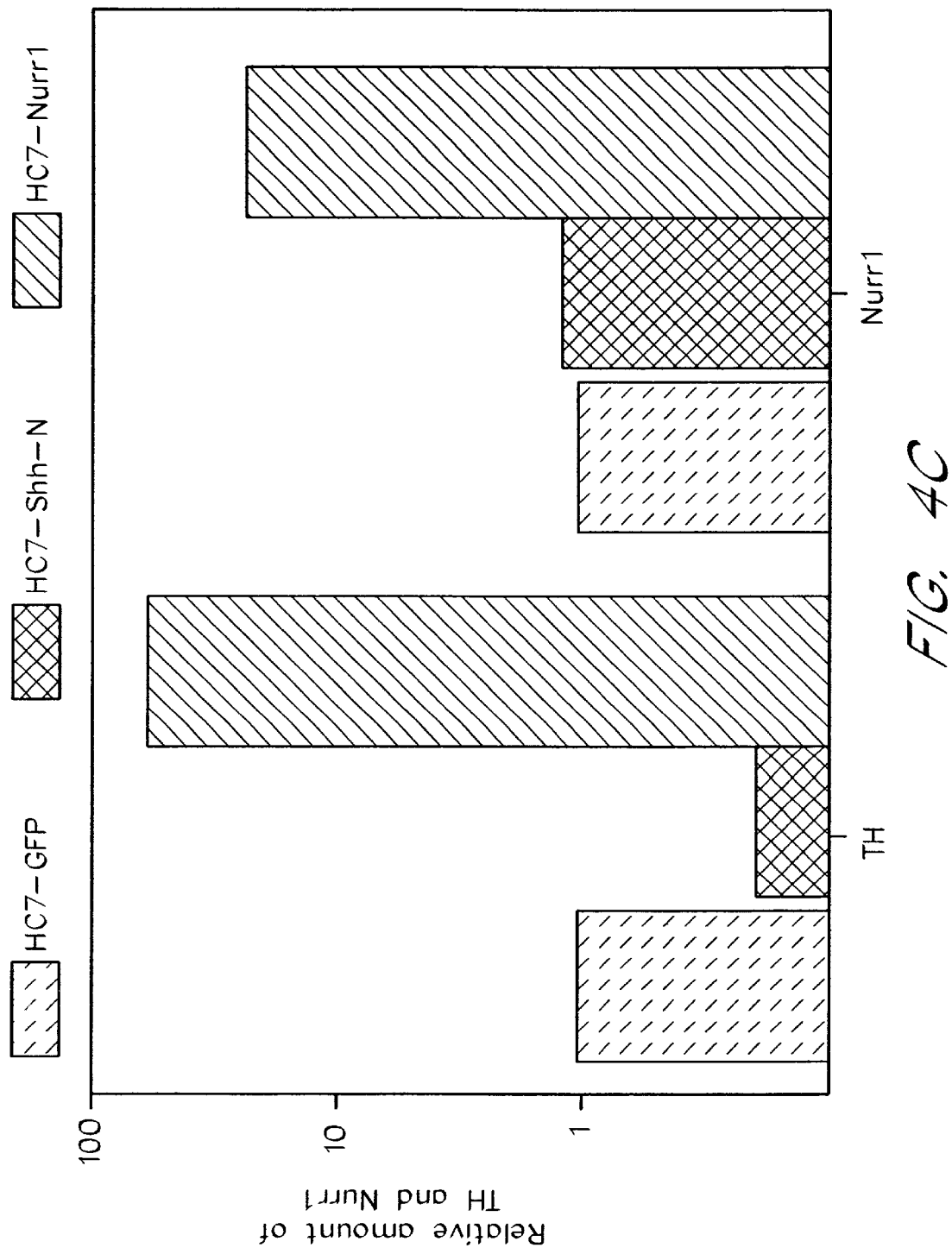
Figure 5:
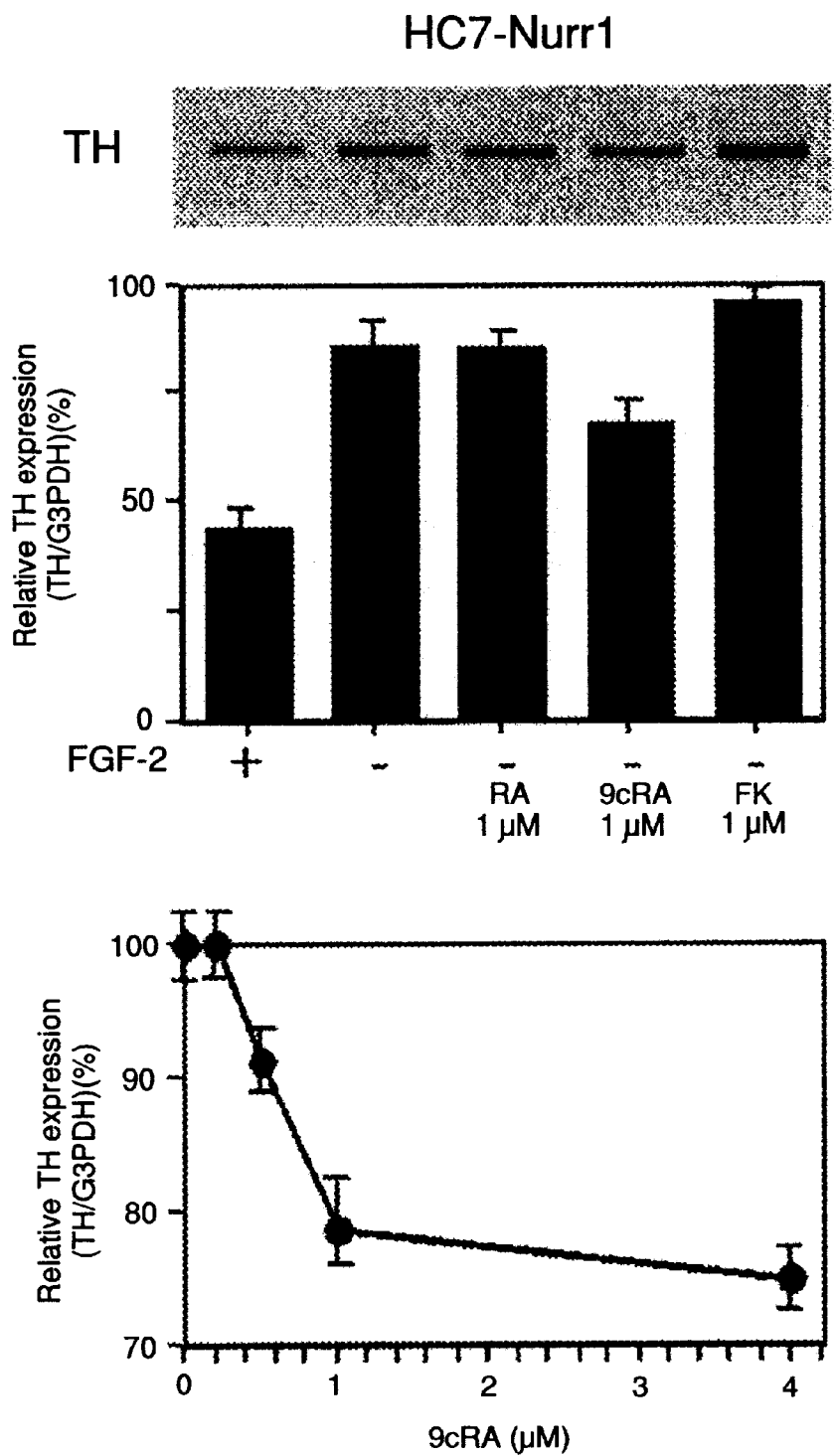
FIG. 5 is a diagram depicting the expression of TH by HC7-Nurr1 cells cultured in the indicated condition for 24 hours. FGF-2+indicates proliferating conditions, and FGF-2− indicates differentiating conditions triggered by FGF-2 withdrawal.
Figure 6C:
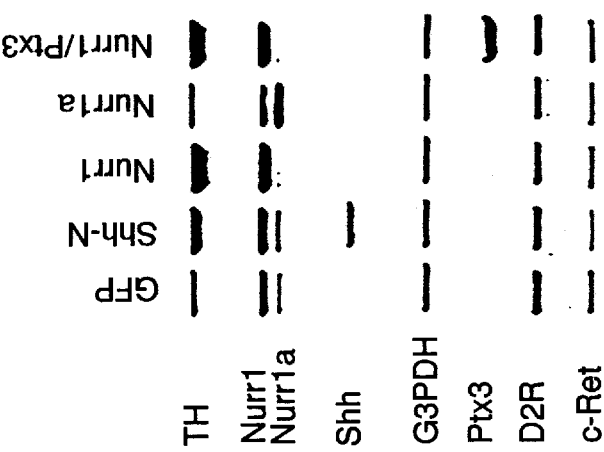
FIG. 6C shows RT-PCR products generated from total RNA isolated from HC7 cells infected with retroviruses (NIT) expressing GFP, Shh-N, Nurr1, or Nurr1a, selected in G418 for ten days without tetracycline, and induced to differentiate in the presence of FK. Nurr1/Ptx3 cells represents stable HC7-Nurr1 cells transiently expressing Ptx3.
Figure 6B:
FIG. 6B shows RT-PCR products generated from total RNA isolated from HC7 cells infected with retroviruses (NIT) expressing GFP, Shh-N, Nurr1, or Nurr1a, selected in G418 for ten days without tetracycline, and induced to differentiate in the presence of RA.
Figure 6A:
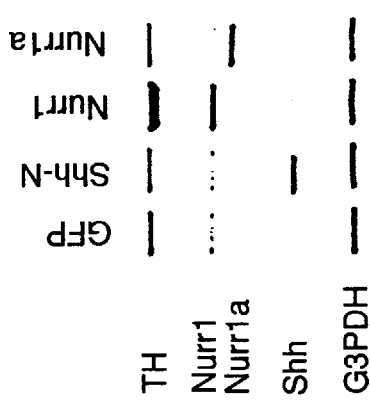
FIG. 6A shows RT-PCR products generated from total RNA isolated from C31 cells infected with retroviruses (RVEN3) expressing GFP, Shh-N, Nurr1, or Nurr1 a transiently, and induced immediately to differentiate in the presence of RA.
Figure 6D:
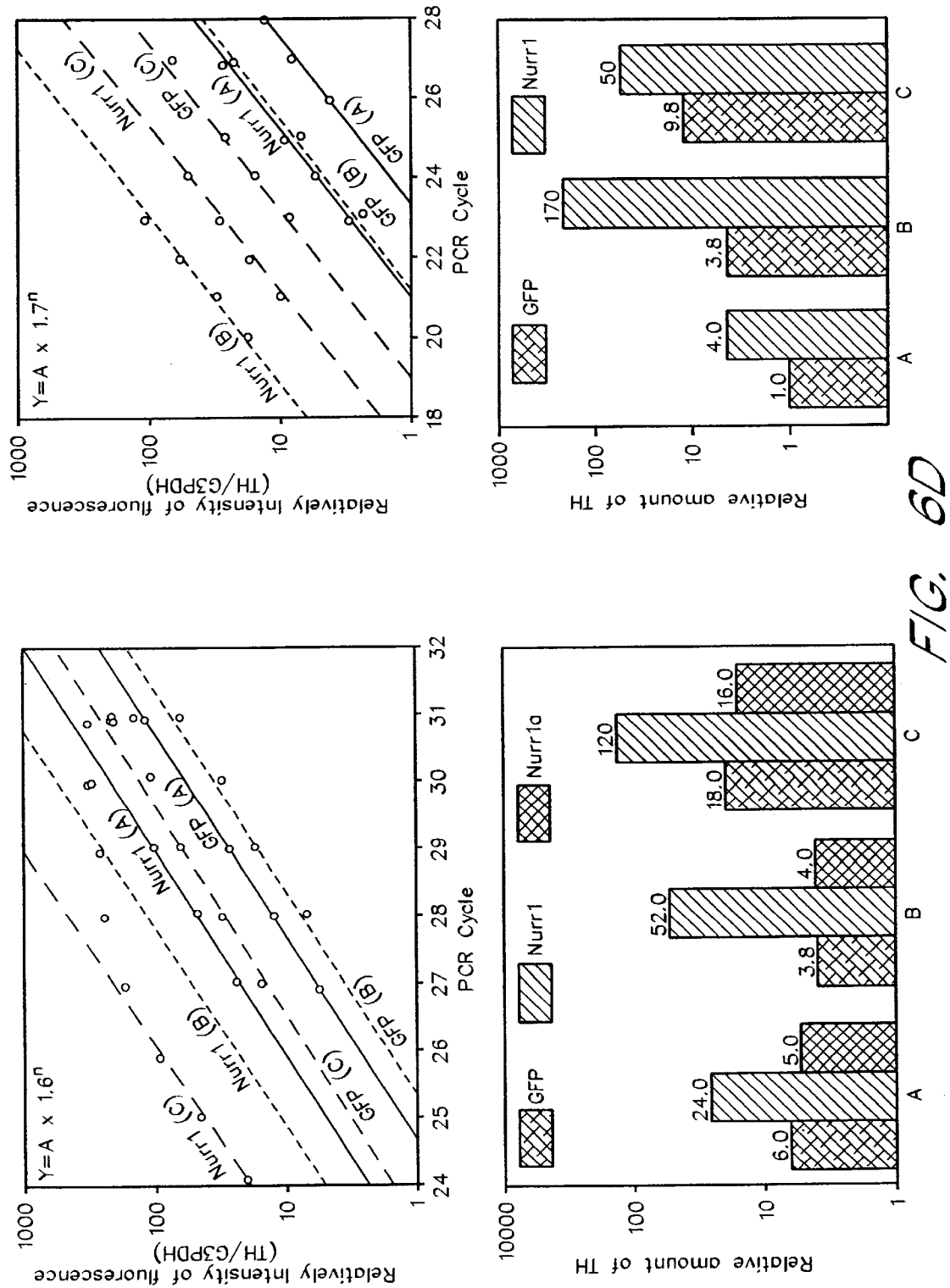
FIG. 6D shows quantification of TH and Nurr1 transcripts in Nurr1, Nurr1a and GFP overexpressing cells shown in A–B above. Sequential cycles of RT-PCR were performed with total RNA used in (A), (B) and (C). Relative intensity of fluorescence on PCR products stained by EtBr is plotted as a function of PCR cycle. Relative amounts of Nurr1 and TH transcripts were obtained from RT-PCR kinetics analyses shown in top two panels. Kinetic analysis were performed as described in the specification.

The roles of Nurr1 and Nurr1a (a COOH-terminal truncation of Nurr1 formed by alternative splicing) were examined. Nucleic acid encoding these polypeptides were subcloned into the retrovirus expression vectors NIT or RVEN3, and the resulting vectors used to transduce AHPs cultures (FIG. 2). Nurr1-expressing retrovirus (NIT-Nurr1) was introduced into AHPs and a bulk population of stable Nurr1-expressing cells (HC7-Nurr1) was isolated by G418 selection. Nurr1 mRNA was expressed at 25-fold higher levels than in non-transduced controls, and TH expression was elevated 60-fold in proliferating cells (FIG. 4). In addition, the 60-fold increase in TH expression was maintained during the rapid induction of TH observed in response to FGF-2 withdrawal and FK treatment. For example, at 24 hours following FGF-2 withdrawal, both control and Nurr1-expressing cells exhibited a 2-fold increase in TH expression but the absolute level of TH expression remained 60-fold higher in Nurr1-expressing cells compared to non-infected controls (FIG. 5). By six days, this differential TH response was maintained but to a lesser extent. TH expression was 14-fold or 7-fold higher in Nurr1-expressing cells than in non-infected controls in the presence of RA and FK, respectively (FIG. 6). Interestingly, Nurr1 had little effect on the proliferation of cells, and expression levels of Ptx3, AADC, c-Ret, and GFR-α1 were not affected. In other words, forced expression of Nurr1 did not alter the proliferative state of the cells. Similar results were obtained using the stem cell-derived C31 line.

Overexpression of Nurr1a, the COOH-terminal truncated form of Nurr1, had little effect on TH expression, either in proliferating or differentiating cells (FIGS. 4–6). These results indicate that the alternatively spliced form of Nurr1 does not function to activate TH expression. In addition, the forced expression of Nurr1a did not negatively regulate the Nurr1 activation of TH expression in either control cells expressing endogenous levels of Nurr1 or HC7-Nurr1 overexpressing cells.

Forced expression of Nurr1 alone was not sufficient to induce TH expression in fibroblast and kidney cell lines. Specifically, the full length Nurr1 was introduced into the rat primary skin fibroblast cell line (FF12) and the human kidney cell line (293 cells) using the RVEN3 retroviral vector. In both cases, TH expression was not detected.

In addition, TH polypeptide expression was examined by immunofluorescent staining. TH immunoreactivity was detected ubiquitously in HC7-Nurr1 cells in both proliferating and differentiating conditions. In addition, TH polypeptide was detected at low levels in all Nurr1-expressing cells; however, following differentiation in either RA or FK, TH expression was markedly upregulated in roughly 1% of the Map2ab-positive neurons. These strongly TH immunoreactive neurons were generated at similar numbers even in the absence of forced expression of Nurr1. These results indicate that Nurr1 overexpression can activate TH expression in undifferentiated cells yet not to the extent achieved during a fully activated neuronal differentiation program.

The Nurr1-induced expression of TH resulted in the synthesis of active TH enzyme. Cell lysates were analyzed for DOPA, dopamine, and DOPAC by reverse-phase high-performance liquid chromatography (HPLC). Briefly, cells were collected after 6 days of differentiation in N2 medium supplemented with FK or after 2 days of proliferation in the presence of FGF-2, and suspended in lysis buffer containing 100 mM perchloric acids, 50 mM EDTA pH 8.0, and 50 mM sodium bisulfate. Samples were freeze/thawed twice and supernatants were collected by centrifugation at 14,000 rpm for 5 minutes. These samples were assayed for DOPA, dopamine, and DOPAC using reverse phase HPLC with electrochemical detection as described elsewhere (Melega et al., *Brain Res.* 543:271–276 (1991)).

Figure 7A:
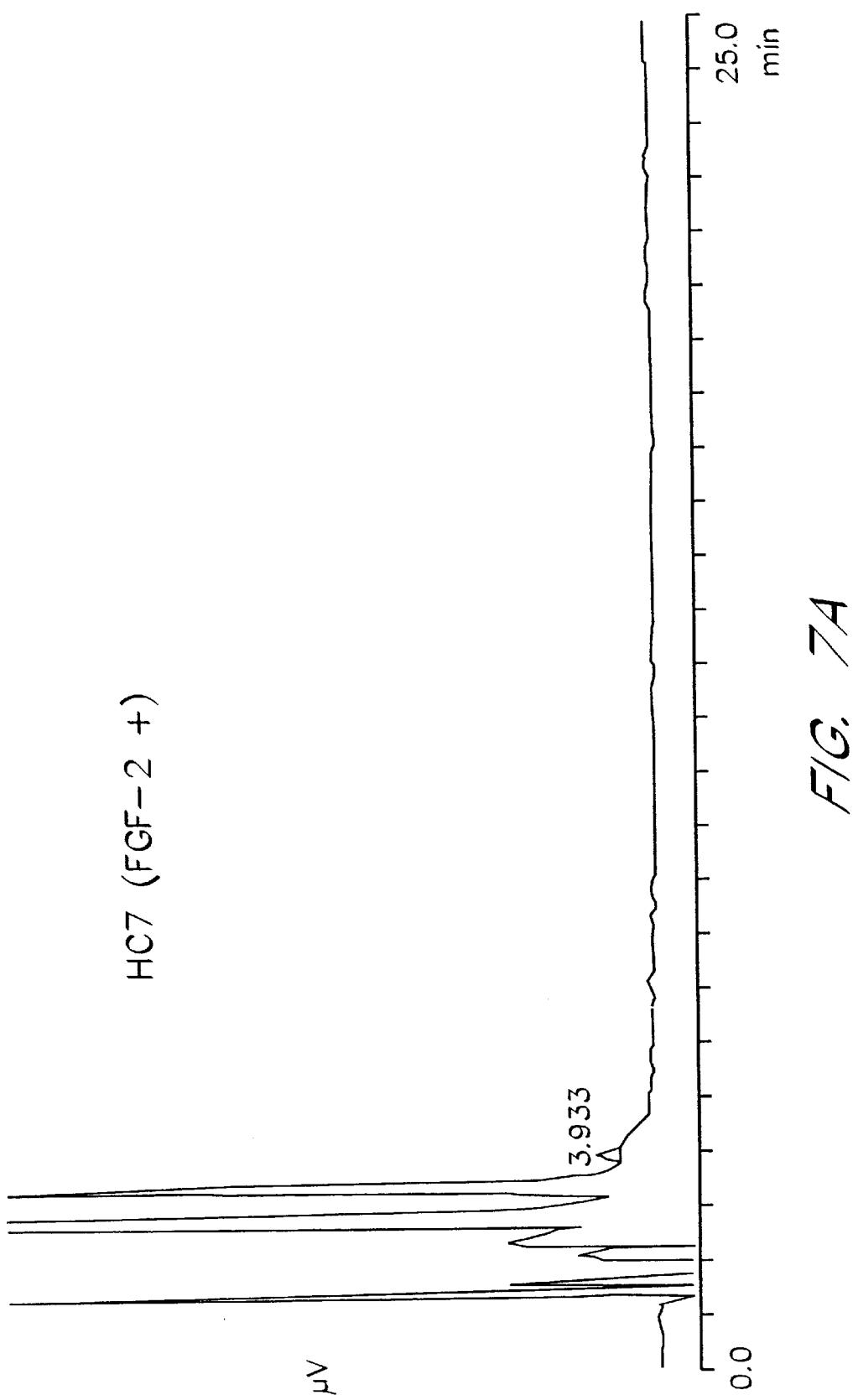
FIG. 7A shows a HPLC chromatogram of a cell lysate from HC7 cells propagated with FGF-2.
Figure 7B:
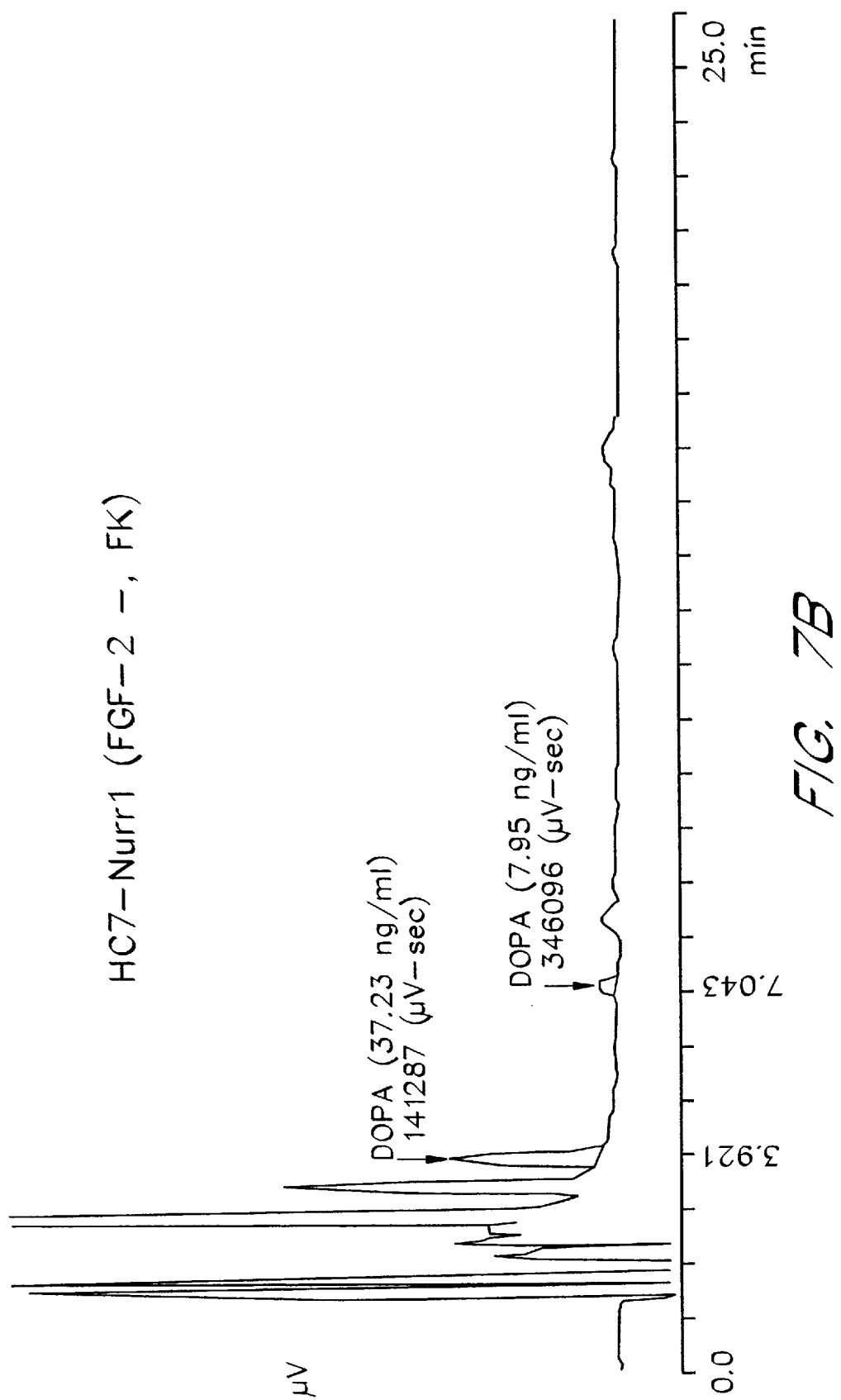
FIG. 7B shows a HPLC chromatogram of a cell lysate from HC7-Nurr1 cells differentiated in the presence of FK.

DOPA and DOPAC were detected in HC7-Nurr1 cell lysates after 6 days of differentiation in the presence of FK (FIG. 7). The total amounts of DOPA and DOPAC were 49.2 ng/mg protein. Control HC7 cells did not produce detectable amounts of DOPA or DOPAC. These results indicate that the TH expression detected in Nurr1-expressing cells led to the production of functional TH enzyme. In addition, since DOPA is rapidly converted to dopamine by AADC and is subsequently converted to DOPAC by MAO and aldehyde dehydrogenase, the presence of DOPAC indicates that both TH and AADC are functional.

5. Ptx3 Had Little Effect on Proliferation and Differentiation

The role of Ptx3 during proliferation and differentiation was examined. Nucleic acid encoding this polypeptide was subcloned into the retrovirus expression vector RVEN3, and the resulting Ptx3-containing expression vector was used to transduce Nurr1-stable cells (HC7-Nurr1). Ptx3 mRNA was easily detected in these cells; however, the expression of TH, AADC, c-Ret, GFRα-1, and D2R was not affected (FIGS. 4 and 6).

Since Ptx3-expressing cells may require Nurr1 for survival, HC7 cells were treated with a GFP-tagged retroviral vector (GIT) expressing Ptx3 so that individual Ptx3-expressing cells can be followed in a population of cells that express very low levels of endogenous Nurr1 (FIG. 1). No differences in proliferation or differentiation relative to GFP expression alone were observed, indicating that Ptx3 overexpression does not itself induce apoptosis in cells expressing low levels of Nurr1.

Example 4

Nurr1 Polyoeptide Binds Directly to a Nurr1 Binding Element Within the TH Promoter Six kilobases of sequence upstream of the TH start site were scanned for putative Nurr1 binding sites. DNase I footprint analysis was performed using recombinant Nurr1 polypeptide and a DNA fragment corresponding to the rat Th promoter positions −962 to −729. Briefly, labeled TH DNA fragments (−962 to −729) used for footprint analysis were generated by PCR using a plasmid containing 4.5 kb of the rat TH promoter as template (provided by Chikaraishi) and two oligo primers, one of which was $^{32}P$ end-labeled. The resulting PCR products were gel purified using 6% polyacrylamide gel. Nurr1 polypeptide was produced in a TNT coupled reticulocyte lysate system (Promega). DNase I footprint reactions were carried out in 25 mM HEPES-KOH pH 7.5, 80 mM potassium chloride, 1 mM magnesium chloride, 20% glycerol, 0.05% NP-40, and 5% polyvinyl alcohol with a fixed amount of reticulocyte lysate. Dose response experiments were performed using different ratios of unreacted and reacted reticulocyte lysate. For example, the end-labeled fragments were incubated with 0, 10, 5, and 1 µl of reticulocyte lysate reaction mixture of Nurr1 polypeptide combined with 10, 0, 5, and 9 µl of unreacted reticulocyte lysate, respectively. DNase I digestions were carried out with 0.1 unit of enzyme at room temperature for one minute. DNA sequencing was performed by the same labeled primer using Sequenase kit (Amersham).

Titration of Nurr1 polypeptide gave progressive protection of nucleotides spanning positions −873 to −866 (5'-AAAGGTCA-3';). In contrast, Nurr1a exhibited only weak protection at the same site. Taken together, these data indicate that Nurr1 activates TH expression by binding directly to a midbrain dopaminergic neuron-specific enhancer element of the TH promoter.

To determine whether Nurr1 acts in a 9cRA-dependent or 9cRA-independent manner to induce TH expression, the effects of 9cRA on TH expression were examined. HC7-Nurr1 cells were exposed to FGF-2 withdrawal and treatment with 9cRA for 24 hours. FGF-2 withdrawal increased TH expression 2-fold. Addition of all-trans RA (RA) had no additional effect on TH expression at this very early time in differentiation. In contrast, TH expression decreased in the presence of 9cRA in a dose-dependent manner (FIG. 5). These results indicate that the activating effects of Nurr1 on TH expression are not dependent on 9cRA.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A cell comprising exogenous nucleic acid, said exogenous nucleic acid comprising a nucleic acid sequence that encodes an amino acid sequence, wherein said nucleic acid sequence comprises the sequence set forth in SEQ ID NO: 1, wherein said amino acid sequence is expressed and induces tyrosine hydroxylase expression within said cell.

2. The cell of claim 1, wherein said cell is a mammalian cell.

3. The cell of claim 2, wherein said cell is derived from an adult mammal.

4. The cell of claim 1, wherein said cell is a neural progenitor cell.

5. The cell of claim 4, wherein said cell is a midbrain neural progenitor cell.

6. The cell of claim 4, wherein said cell is a neural cell.

7. The cell of claim 1, wherein said cell expresses at least one polypeptide selected from the group consisting of Otx1, En1, and Ptx3.

8. The cell of claim 1, wherein said tyrosine hydroxylase expression promotes DOPA production in said cell.

9. The cell of claim 1, wherein said tyrosine hydroxylase expression promotes dopamine production in said cell.

10. The cell of claim 1, wherein said tyrosine hydroxylase expression promotes norepinephrine and epinephrine production in said cell.

* * * * *